(12) United States Patent
Kellar et al.

(10) Patent No.: US 12,419,719 B2
(45) Date of Patent: Sep. 23, 2025

(54) CAMERA APPARATUS FOR COORDINATED OPERATION WITH SURGICAL TOOLS

(71) Applicant: Arthrex, Inc., Naples, FL (US)

(72) Inventors: Ryan Kellar, Naples, FL (US); James Kitchen, Fort Myers, FL (US); Andrew Melton, Santa Barbara, CA (US); Tzung-Yu Hsu, Taoyuan (TW); Rachel M. Frank, Denver, CO (US); Chad Lavender, Hurricane, WV (US); Benjamin Siegel, Naples, FL (US); Erik Jamison-Ekeling, Lino Lakes, MN (US); Connor Engstrom, Ventura, CA (US); Craig Speier, Santa Barbara, CA (US); Robert Fergan, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 18/599,415

(22) Filed: Mar. 8, 2024

(65) Prior Publication Data

US 2024/0299123 A1 Sep. 12, 2024

Related U.S. Application Data

(60) Provisional application No. 63/451,251, filed on Mar. 10, 2023.

(51) Int. Cl.
*A61B 90/00* (2016.01)
*G06T 1/00* (2006.01)
*G16H 30/20* (2018.01)

(52) U.S. Cl.
CPC .......... *A61B 90/361* (2016.02); *G06T 1/0007* (2013.01); *G16H 30/20* (2018.01)

(58) Field of Classification Search
CPC .............. A61B 90/361; A61B 1/00066; A61B 1/00112; A61B 1/00121; A61B 1/313; A61B 1/3132; A61B 1/317; A61B 1/0014; G06T 1/0007; G16H 30/20
See application file for complete search history.

(56) References Cited

U.S. PATENT DOCUMENTS

| 5,833,611 | A | 11/1998 | Tepper et al. |
| 8,961,407 | B2 | 2/2015 | Piskun et al. |
| 9,918,617 | B2 | 3/2018 | Viola et al. |
| 11,331,120 | B2 | 5/2022 | Hansen et al. |
| 11,369,253 | B2* | 6/2022 | Truckai ............... A61B 1/0008 |
| 2008/0159653 | A1* | 7/2008 | Dunki-Jacobs ........ A61B 5/067 382/293 |
| 2012/0040305 | A1 | 2/2012 | Karazivan et al. |

(Continued)

*Primary Examiner* — Brent D Castiaux
(74) *Attorney, Agent, or Firm* — Price Heneveld LLP

(57) ABSTRACT

A surgical imaging system includes at least one camera apparatus having a camera body including an image sensor configured to capture image data in a field of view. A scope extends along a longitudinal axis from the camera body. A camera orientation sensor is in connection with the camera apparatus. The camera orientation sensor detects a camera orientation of the camera apparatus. A scope orientation sensor detects a scope orientation of the scope relative to the camera body. A controller monitors the camera orientation and the scope orientation. In response to a change in the scope orientation relative to the camera orientation, the controller updates a rotation of the field of view of the image data.

23 Claims, 13 Drawing Sheets

(56) References Cited

U.S. PATENT DOCUMENTS

| | | |
|---|---|---|
| 2017/0252056 A1 | 9/2017 | Garvey et al. |
| 2018/0354442 A1* | 12/2018 | Bergstrom ................ B60R 1/06 |
| 2019/0015254 A1 | 1/2019 | Bendory et al. |
| 2022/0000341 A1 | 1/2022 | Zhang |
| 2022/0125283 A1 | 4/2022 | Kress |

* cited by examiner

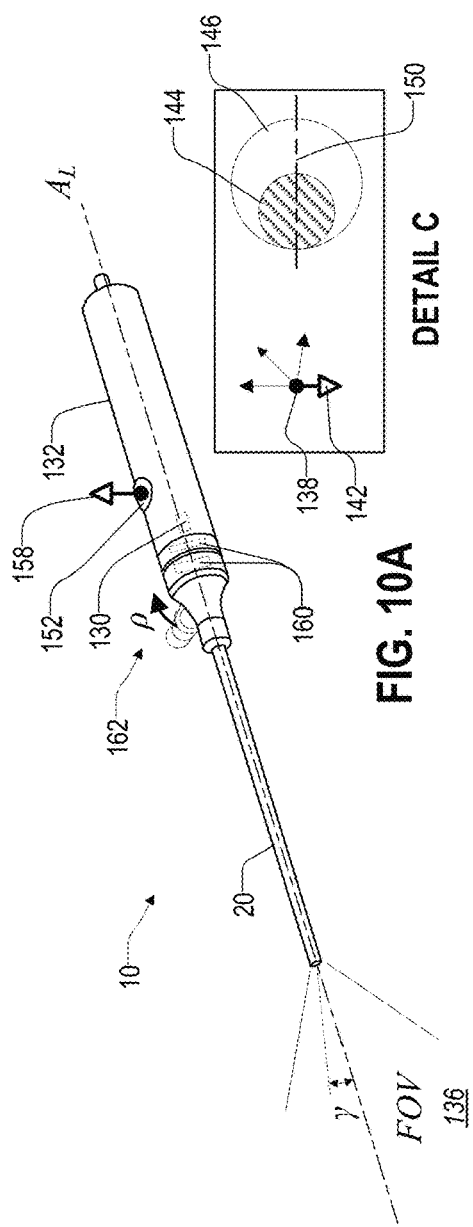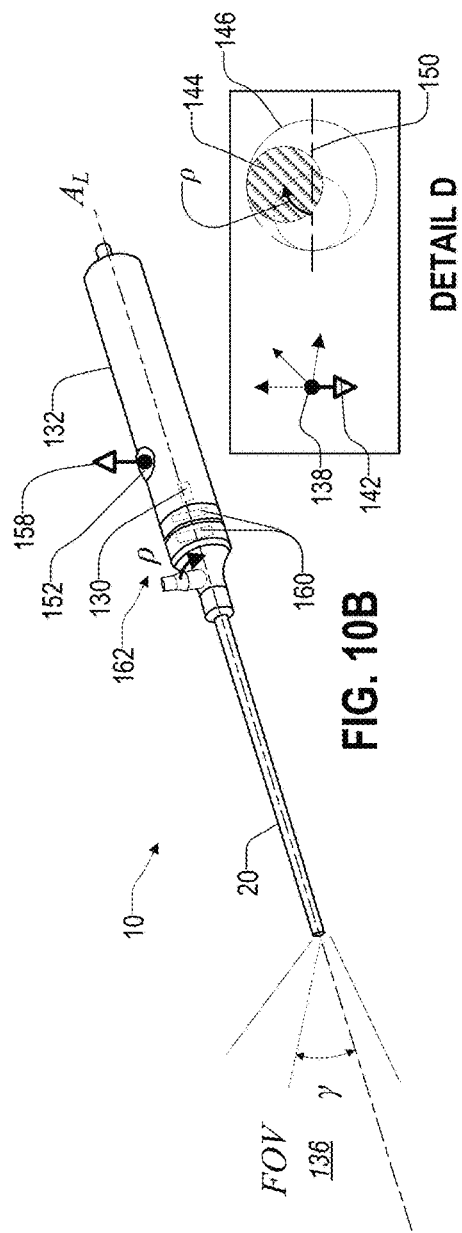

CAMERA APPARATUS FOR COORDINATED OPERATION WITH SURGICAL TOOLS

CROSS-REFERENCE TO RELATED APPLICATIONS

This application claims priority under 35 U.S.C. § 119(e) and the benefit of U.S. Provisional Application No. 63/451,251 entitled CAMERA APPARATUS FOR COORDINATED OPERATION WITH SURGICAL TOOLS, filed on Mar. 10, 2023, by Kellar et al., the entire disclosure of which is incorporated herein by reference.

BACKGROUND

The present disclosure generally relates to a camera apparatus or camera probe for surgical applications and, more particularly, relates to a camera apparatus having one or more features for coordinated operation with surgical tools. The operation of camera probes (e.g., endoscopes, arthroscopes, laparoscopes, etc.) may require manual manipulation in combination with the manipulation and operation of surgical tools utilized for various patient procedures. Such manipulation may create challenges, particularly when viewing narrow patient cavities as commonly necessitated by minimally invasive surgical procedures. The following disclosure provides for a variety of features and associated operating methods to improve the operation of surgical imaging devices and the related presentation of image data demonstrating various anatomical features and tools to assist in surgical procedures.

SUMMARY

In general, the disclosure provides for a camera apparatus, related features and operating methods that may improve the coordinated operation of one or more cameras or camera probes in combination with surgical tools. In various implementations, the camera apparatus may be configured to operate in connection with surgical tools, including elongated shafts that may be implemented to access internal patient cavities for minimally invasive surgical procedures. For example, in some cases, the disclosure may provide for a surgical imaging system including one or more cameras or camera apparatuses. The camera apparatuses may include a camera orientation sensor and/or a scope orientation sensor. The camera orientation sensor may be configured to identify spatial orientations of the camera apparatuses, for example relative to gravity. Additionally, the scope orientation sensor may be configured to detect a rotation or scope orientation of the scope relative to a camera body of the camera apparatus. By monitoring the relationship of the camera orientations among the cameras, as well as the scope orientation, a controller coordinates the display of multiple, corresponding video feeds, which may depict different portions of an internal cavity of a patient.

In some implementations, the disclosure may provide for a detection of a horizon direction of one or more of the camera apparatuses with respect to gravity. For example, the scope orientation or a rotation angle of the scope relative to the camera body may be monitored and updated to rotate the image data captured by one or more of the camera apparatuses. By monitoring the orientation of the camera with respect to gravity and the rotation of the scope, the subject matter presented in the field of view may be maintained with respect to the horizon even as the rotation angle of the scope is adjusted. As provided in further detailed examples throughout the following description, the camera orientation and/or scope orientation of one or more camera apparatuses may be received by the surgical imaging system to adjust a variety of angular relationships, viewing parameters, and/or select the display of image data received from each of the camera apparatuses. In this way, the disclosure may provide for automated or assisted viewing of one or more fields of view for presentation on a display.

These and other features, objects and advantages of the present disclosure will become apparent upon reading the following description thereof together with reference to the accompanying drawings.

BRIEF DESCRIPTION OF THE DRAWINGS

FIG. 10A is an illustrative projected view of a camera apparatus demonstrating a first camera orientation and a first scope orientation;

FIG. 10B is an illustrative projected view of a camera apparatus demonstrating the first camera orientation and a second scope orientation;

DETAILED DESCRIPTION

Figure 1:
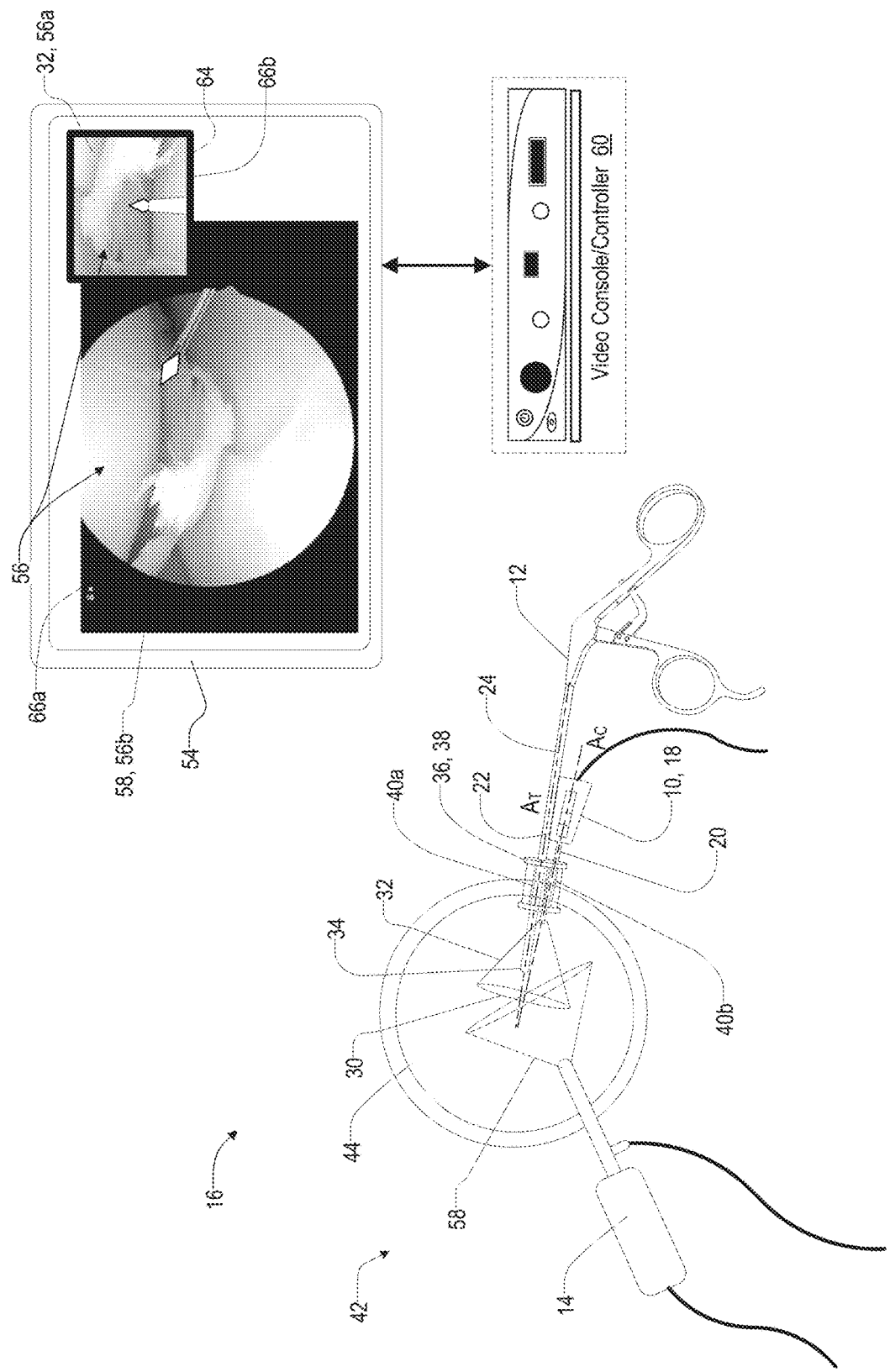
FIG. 1 is an illustrative diagram demonstrating a camera apparatus of a surgical imaging system.

In the following description, reference is made to the accompanying drawings, which show specific implementations that may be practiced. Wherever possible, the same reference numbers will be used throughout the drawings to refer to the same or like parts. It is to be understood that other implementations may be utilized and structural and functional changes may be made without departing from the scope of this disclosure.

Referring to FIGS. 1-4, in various implementations, the disclosure may provide for a camera apparatus or imaging device 10 designed for improved operation in coordination with at least one of a surgical tool 12 and an endoscope 14 (e.g., a camera probe, arthroscope, laparoscope, etc.) forming a surgical imaging system 16. As demonstrated in FIG. 1, the camera apparatus 10 may include a body 18 or enclosure in connection with a camera probe 20. The body 18 or enclosure of the camera apparatus 10 may include at least one support surface 22 that may control a spacing Hs and intersection angle θ between a shaft 24 of the surgical tool 12 and the camera probe 20. When implemented in combination, the support surface 22 of the body 18 may control an intersection distance $D_{int}$ that may generally be defined by an intersection of the tool axis $A_T$ with a focal region 30 of the camera apparatus 10 positioned at a working distance $L_f$ beyond a distal end portion 20b of the camera probe 20. In this configuration, the support surface 22 formed by the body 18 and the camera apparatus 10 may align a field of view 32 and focal region 30 of the camera probe 20 with a working end 34 or actuator of the surgical tool 12 at the intersection distance $D_{int}$.

The camera apparatus 10 may be configured to maintain an alignment between the shaft 24 of the surgical tool 12 by holding the support surface 22 in connection with the shaft 24 via a collar 36 or retention strap enclosed around and/or connecting at least a portion of the camera apparatus 10 to the shaft 24. In the example shown, the collar 36 forms a portion of a cannula 38 or access port. The cannula 38 may include at least one lumen 40 through which the shaft 24 of the surgical tool 12 and the probe 20 of the camera apparatus 10 may extend from an exterior environment 42 into a patient cavity 44. In this configuration, the at least one lumen 40 formed by the collar 36 of the cannula 38 may be enclosed about at least a portion of the shaft 24 and the camera apparatus 10, such that the support surface 22 is compressed and retained in contact with the shaft 24, thereby aligning the tool axis $A_T$ with the intersection angle θ defined by the support surface 22.

Figure 2:
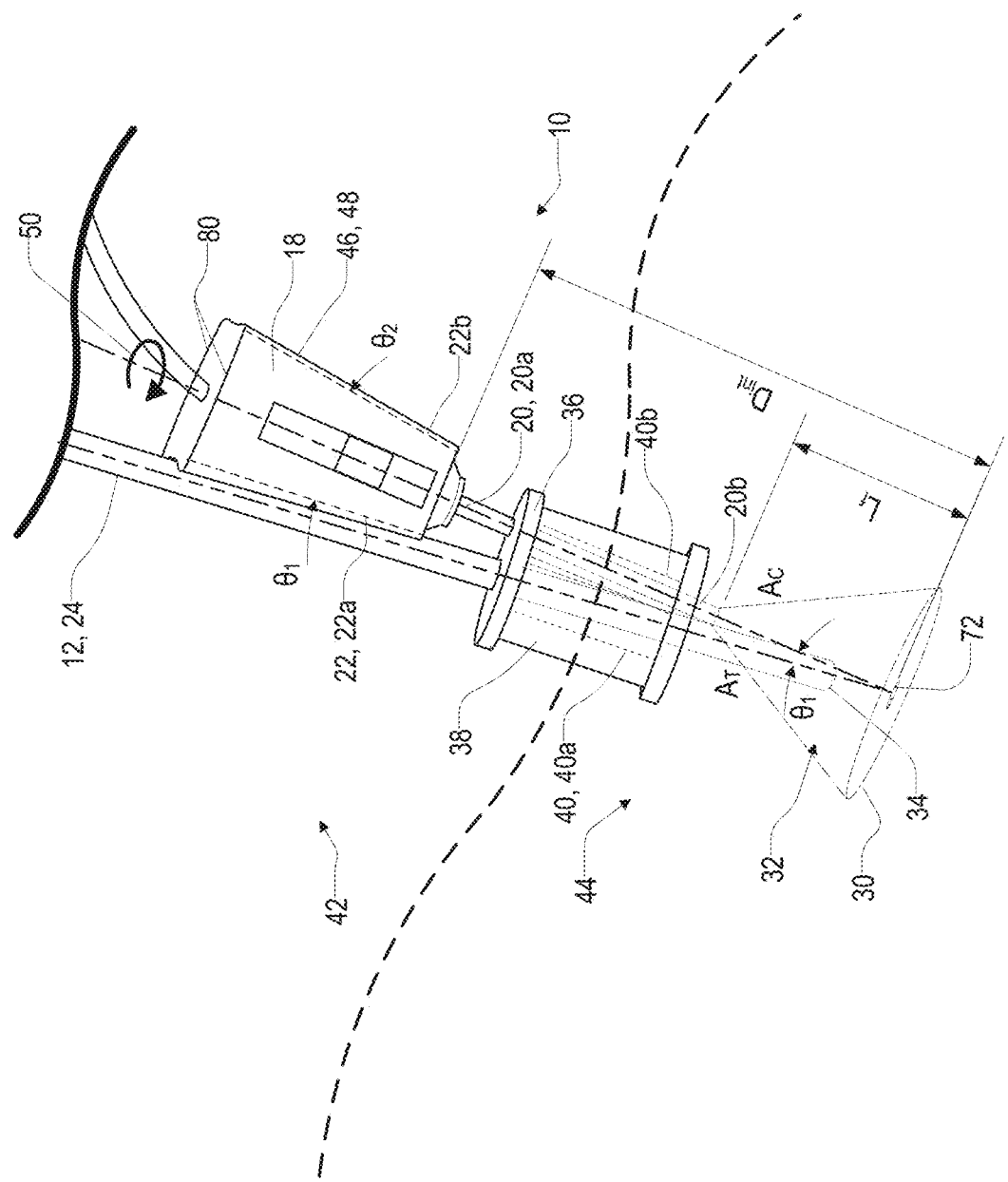
FIG. 2 is a projected view of a camera apparatus implemented in combination with a surgical tool.

As best shown in FIGS. 1 and 2, the cannula 38 may comprise a first lumen 40a and a second lumen 40b configured to receive the shaft 24 and the probe 20, respectively. In various implementations, the cannula 38 and/or collar 36 may be formed of a flexible or elastically deformable material (e.g., silicone, rubber, or various similar elastomeric materials, etc.). When used in combination with the camera apparatus 10 and the tool 12 oriented along the intersection cannula 38 and/or collar 36, the elastic material of the cannula 38 and/or collar 36 may be stretched outward. In response to the stretching, the elastic nature of the cannula 38 and/or collar 36 may apply a compressive force to the shaft 24 and the camera apparatus 10, such that the shaft 24 may be retained within a depression 46 or channel 48 formed by the support surface 22 and aligned relative to the camera probe 20 along the intersection angle θ. In this configuration, the pressure applied to the shaft 24 by the collar 36 and/or cannula 38 may allow surgical tool 12 to be manipulated and/or maneuvered with the camera apparatus 10 retained in constant relative position and orientation to the surgical tool 12 throughout the associated movements.

Figure 3:
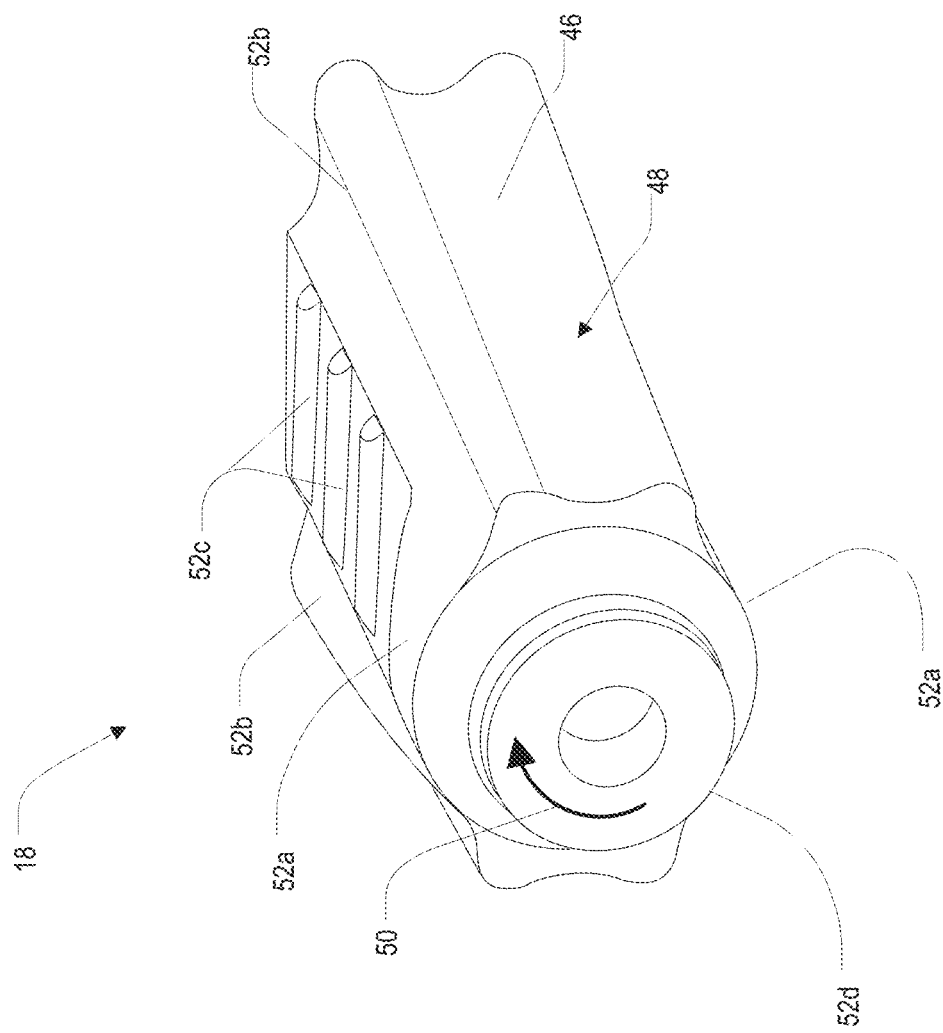
FIG. 3 is a projected view demonstrating a body or enclosure of a camera apparatus defining an intersection of angle of a camera probe.

As best shown in FIG. 3, the support surfaces 22 may correspond to alignment features or positive spacing features forming an angled wedge or otherwise spacing and angling the camera axis $A_C$ relative to the tool axis $A_T$ at the intersection angle θ. The depressions 46 formed by the channels 48 may correspond to elongated troughs, guides, or retention features that may maintain the angular spacing of the camera axis $A_C$ relative to the tool axis $A_T$ by preventing a change in a rotational orientation 50 of the camera apparatus 10 relative to the surgical tool 12. In the example shown, the body 18 may correspond to an interface adapter that may include opposing interface surfaces 52a extending outward from the camera axis $A_C$ over opposing wings 52b between the support surface 22. In this configuration, the interface surfaces 52a may provide semi-flattened surfaces for gripping and adjusting the orientation of the body 18, which may include a textured surface, ridges 52c, gripping elements, or similar features to improve tactile interaction. The probe 20 is hidden from the view of the body 18 for clarity. However, a flange 52d of the body 18 may interconnect with the proximal end portion of the probe 20a and may extend along the camera axis $A_C$ beyond the extent of the support surface(s) 22.

Referring again generally to FIGS. 1-4, in various implementations, the combined interaction of the camera apparatus 10 and the surgical tool 12 with the cannula 38 and/or collar 36 may further allow the camera apparatus 10 to be manipulated and rotated about the camera axis $A_C$ relative to the position and orientation of the surgical tool 12 and the shaft 24 as represented by the arrow 50. In this way, the orientation of the camera apparatus 10 may be adjusted and rotated relative to the orientation and position of the surgical tool 12 and selectively coupled to the surgical tool, such that the camera apparatus 10 maintains a constant orientation to the surgical tool 12 at the intersection angle θ. As discussed in various examples throughout the following detailed description, the selective control of the relative movement between the camera apparatus 10 and the surgical tool 12 may be particularly beneficial in adjusting the orientation of the body 18. For example, in some implementations, adjusting the angular orientation of the body 18 relative to the surgical tool 12 about the camera axis $A_C$, may align the shaft 24 with one of a plurality of different support surfaces 22 (e.g., a first support surface 22a, a second support surface 22b, etc.), which may vary the intersection angle θ and/or the spacing HS. In this way, the camera apparatus 10 may be used to selectively adjust the intersection distance $D_{int}$ and/or the perspective of the working end 34 demonstrated in the field of view 32. Examples of the camera apparatus 10 having a plurality of different support surfaces 22 are further described and demonstrated in FIGS. 6A-6E.

Figure 4:
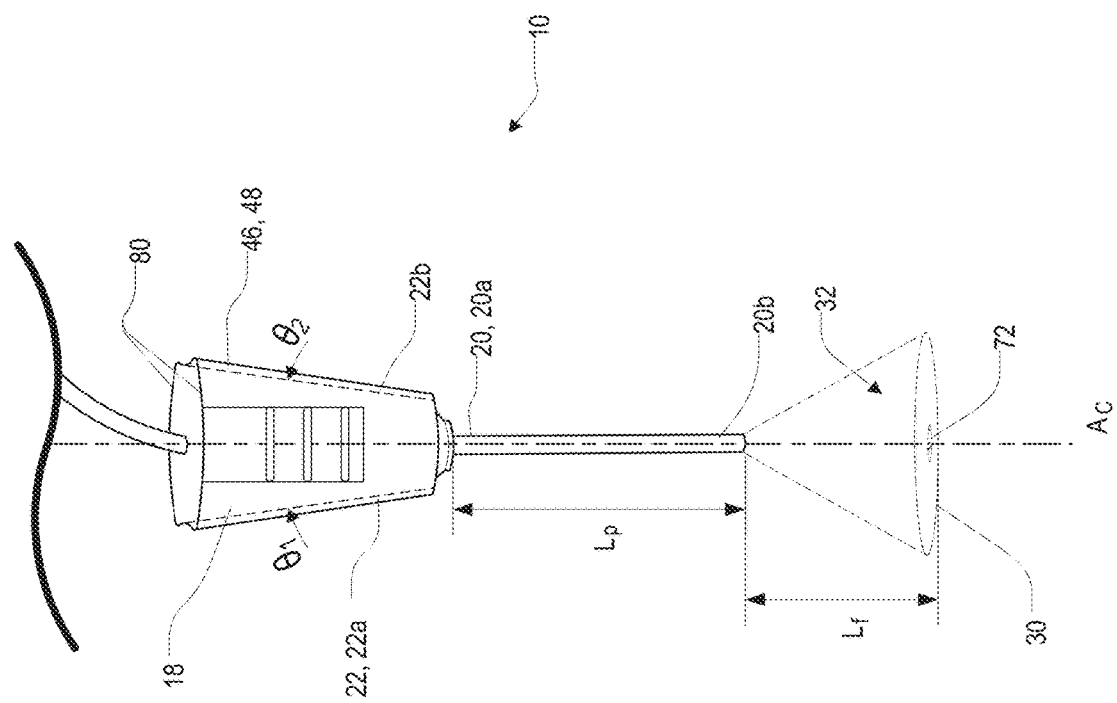
FIG. 4 is a projected view of a camera apparatus demonstrating a focal region defined by a probe length and working distance.

As best shown in the example demonstrated in FIG. 4, the body 18 of the camera apparatus 10 may comprise a first support surface 22a and a second support surface 22b defining a first intersection angle $θ_1$ and a second intersection angle $θ_2$, respectively. The first and second support surfaces 22a, 22b may be positioned on opposing sides of the body 18 across the camera axis $A_C$ forming an elongated trapezoid having a primary axis extending parallel to the camera axis $A_C$. In the example shown, the intersection angles $\theta_1$, $\theta_2$, as well as the corresponding spacing distances $H_{S1}$, $H_{S2}$ are approximately equal, such that the body 18 comprises two perpendicular planes of reflective symmetry extending about the camera axis $A_C$. In this configuration, the angular relationship of the camera apparatus 10 to the surgical tool 12 may be the same when the shaft 24 is aligned with either the first support surface 22a or the second support surface 22b. Such operation may be convenient and provide for simplified manipulation, however, as further discussed in reference to FIGS. 5 and 6, the body 18 of the camera apparatus 10 may form support surfaces that may vary in number as well as spacing Hs and intersection angles $\theta$ to suit various applications.

Before moving on to additional examples of the body 18 and comprising various configurations of support surfaces 22, the exemplary operation of the camera apparatus 10 in combination with the endoscope 14 and the surgical tool 12 for clarity is described in further detail. Referring back to FIG. 1, the camera apparatus 10 may be implemented to capture image data from a first perspective 56a in the field of view 32. For clarity, the field of view 32 may be referred to as a first field of view 32. Additionally, as previously discussed, the endoscope 14 may be utilized in combination with the camera apparatus 10 to capture additional video or image data in a second field of view 58 demonstrating the patient cavity 44 from a second perspective 56b. Throughout the operation of the imaging system 16, a control console or video controller 60 may receive image data from the corresponding image sensors of the camera apparatus 10 as well as the endoscope 14 and process the image data to depict the first field of view 32 and the second field of view 58 on the display 54. In the example shown, each of the fields of view 32, 58 and the corresponding perspectives 56a, 56b may be arranged and oriented by the controller 60 to depict the corresponding image data in a variety of proportions or locations on the display 54. In this way, the combined operation of the surgical imaging system 16 may concurrently provide a user (e.g., a physician, nurse, assistant, etc.) with a variety of corresponding views demonstrating the patient cavity 44 from a plurality of different perspectives 56. Such operation may improve the effectiveness of the surgical imaging system 16 to facilitate various minimally invasive operations.

Still referring to FIGS. 1-4, as previously discussed and further discussed in later detailed examples, the camera apparatus 10 may incorporate a plurality of support surfaces 22 that may be axially distributed about the camera axis $A_C$ in a variety of angular orientations. For example, as shown in FIGS. 1-4, the support surfaces 22a, 22b are on opposing sides axially oriented 180° apart about the camera axis $A_C$. As provided in later examples, the support surfaces 22 may be angularly spaced at various intervals about the camera axis $A_C$. Accordingly, the orientation of the first field of view 32 as demonstrated in FIG. 1 may rotate in correspondence to the angular orientation of the camera apparatus 10, such that the shaft 24 rotates about a perimeter 64 which may be formed by sides or extents of a viewing window 66. In order to avoid visual complexity associated with changes in the angular orientation of the camera apparatus 10 and the corresponding representation of the surgical tool 12 in the first field of view 32, the controller 60 of the system 16 may be configured to detect the position of the surgical tool 12 and identify the corresponding angle associated with the first perspective 56a. In response to the orientation angle of the camera apparatus 10 relative to the tool 12, the controller may rotate or manipulate the image data demonstrated in the first field of view 32 to consistently represent the surgical tool 12 in a default or preferred relationship to the perimeter 64 formed by the viewing window 66.

In the example shown, the surgical tool 12 extends into the field of view 32 of the camera apparatus 10 from a lower perimeter wall 64a or first angular orientation about the perimeter 64 of the viewing window 66. To determine the rotational orientation 50 of the camera apparatus 10, the controller 60 may identify one or more features of the surgical tool 12 within image data captured in the field of view 32, such as the tool shaft 24 and a corresponding vector or path of the shaft 24 in the image data. Once identified, the one or more features may indicate the rotational orientation 50 of the body 18 and the corresponding support surfaces 22 of the camera apparatus 10 relative to the surgical tool 12. Based on this determination, the controller 60 may reorient or angularly align the image data, such that the surgical tool 12 is consistently depicted in the viewing window 66 having the same default or desired angular orientation regardless of the rotation of the camera apparatus 10 relative to the surgical tool 12. Such an operation may allow the user of the camera apparatus 10 to selectively align the various support surfaces 22 of the body 18 to adjust the intersection angle $\theta$ and/or spacing $A_S$ of the tool shaft 24 relative to the camera probe 20 without altering the desired orientation of the corresponding image data relative to the surgical tool 12 in the field of view 32 demonstrated in the viewing window 66.

In various implementations, the associated algorithms and image processing that may be necessary to identify the relative angular orientation of the camera apparatus 10 to the surgical tool 12 may be simplified because the axial spacing and/or positions of each of the support surfaces 22 may be preconfigured and/or identified by the controller 60 based on a serial number, model, or various identifiers indicating the spacing among the support surfaces 22 of the body 18 relative to the field of view 32. Such information may be valuable to the associated orientation correction algorithm by identifying a few finite positions about the viewing window 66 to anticipate the rotation of the field of view 32 as a result of the rotating orientation of the camera apparatus 10. Such information may allow the controller 60 to resolve the orientation detected in the image data to one of a plurality of known angular orientations 52 (e.g., 60 deg., 90 deg., 120 deg., 180 deg., etc.). Further information describing the operation of the video controller 60 and exemplary underlying processors and techniques are further described in reference to FIG. 12.

Figure 5B:
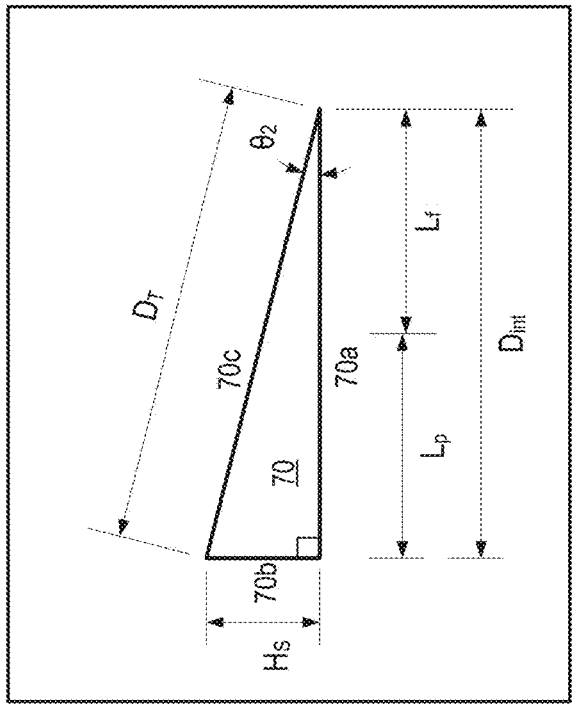
FIG. 5B is a geometric model demonstrating the intersection distance in relation to a probe length and working distance of the camera apparatus demonstrated in FIG. 5A.
Figure 5A:
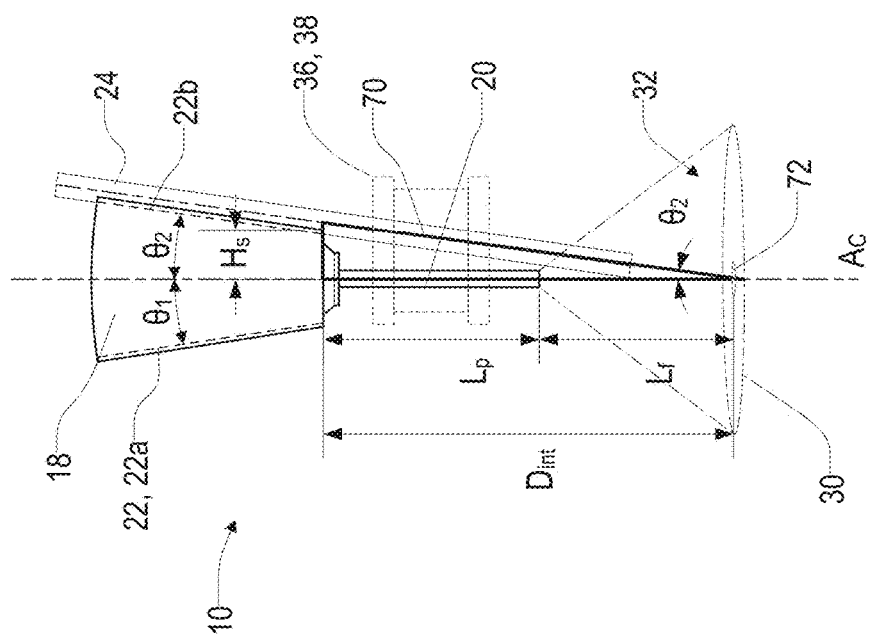
FIG. 5A is a profile view of a camera apparatus demonstrating an intersection distance defined by at least one angled support surface of a body.

Referring now to FIGS. 5A and 5B, the relationship of the intersection angle $\theta$ and spacing distance Hs is further demonstrated and discussed in reference to a geographic model demonstrating a target distance Dr associated with the working end 34 of the surgical tool 12 and the intersection distance $D_{int}$ of the field of view 32. As shown schematically in FIG. 5A, the intersection distance $D_{int}$ may correspond to a sum or combination of the probe distance $L_p$ of the probe 20 and the working distance $L_f$ associated with an optic element or imager disposed at a distal end portion 20b of the probe 20. To clearly demonstrate the relationship and corresponding spacing provided by the camera apparatus 10, a representative triangle 70 is shown in FIG. 5B. Corresponding to the example of the second support surface 22b and the second intersection angle $\theta_2$, a first leg 70a of the triangle 70 is represented by the intersection distance $D_{int}$, which extends from a proximal end 20a of the probe 20 to the focal region 30 or target area 72 at the working distance $L_f$ of the camera apparatus 10. The second leg 70b of the triangle 70 may correspond to the spacing distance Hs between the body 18 of the camera apparatus 10 and the shaft 24 of the surgical tool 12. In this configuration, a hypotenuse 70c of the triangle 70 may correspond to a tool distance Dr or extent of the surgical tool 12 extending beyond the body 18 of the camera apparatus 10 to the working end 34 or actuator. The tool distance Dr in this configuration may define a length of the shaft 24 and working end 34 that may be centrally located within a target area 72 of the field of view 32 of the camera apparatus 10 as depicted in FIG. 5A. However, in various implementations, it may be beneficial to adjust the intersection angle θ and/or the intersection distance $D_{int}$ to accommodate or capture image data better suited to a user preference or operation of surgical tools 12 having variations in geometry, proportions, lengths, etc. Accordingly, some exemplary variations of the geometry of the body 18 and the support surfaces 22 are demonstrated in FIGS. 6A-6E that may be implemented to adjust the operation of the camera apparatus 10 for a variety of applications.

To clearly illustrate the relationship of the intersection distance $D_{int}$ and the tool distance $D_T$ based on the spacing Hs and intersection angle θ, the following equations may define the geometric properties of the camera apparatus 10 to modify and adjust the various relationships described herein to suit a variety of applications. As demonstrated in Equations 1 and 2, the relationships previously described in reference to the triangle 70 are symbolically represented.

$$D_{int} = L_p + L_f \quad \text{(Eq. 1)}$$

$$\tan \theta_2 = (H_s)/D_{int} \quad \text{(Eq. 2)}$$

Based on Equations 1 and 2, the probe length extending from the body 18 of the camera apparatus 10 may be defined by Equation 3.

$$(L_p) = (H_s)/\tan \theta_2 - (L_f) \quad \text{(Eq. 3)}$$

In this way, Equation 3 may be used to identify the probe length based on a known working distance $L_f$ corresponding to the optics or image sensor of the camera apparatus 10 and the desired distance to focal region 30. Similarly, the resulting working distance $L_f$ intersecting with the tool distance $D_T$ or may be calculated based on Equation 4, such that the working distance $L_f$ may be calculated to correspond to a desired presentation of the surgical tool 12, particularly the working end 34, in the field of view 32.

$$(L_f) = (H_s)/\tan \theta_2 - (L_p) \quad \text{(Eq. 4)}$$

Accordingly, the relationships associated with triangle 70 may define at least one example of the operation of the camera apparatus 10.

Figure 6A:
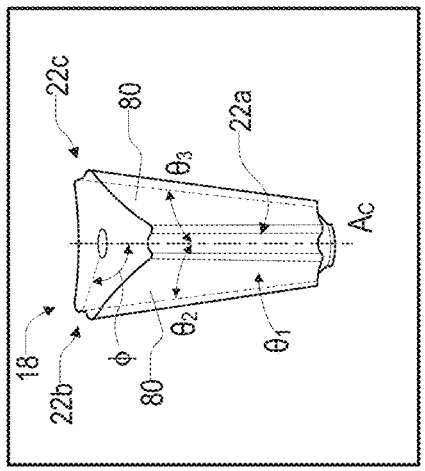
FIG. 6A is a side projected view demonstrating an exemplary implementation of a body of a camera apparatus including a plurality of support surfaces.
Figure 6B:
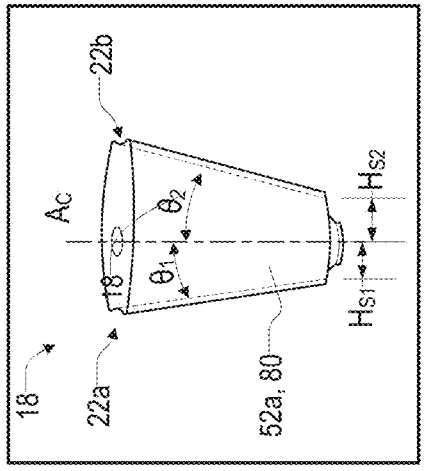
FIG. 6B is a side projected view demonstrating an exemplary implementation of a body of a camera apparatus including a plurality of support surfaces.

Referring now to FIGS. 6A-6E, various examples of the camera apparatus 10 are shown demonstrating variations in intersection angles θ, spacing distances HS, and angular orientations of the support surfaces 22. As shown in FIGS. 6A and 6B, the intersection angles $\theta_1$ and $\theta_2$ of the first support surface 22a and the second support surface 22b may vary alone or in combination with the corresponding spacing distances $H_{S1}$ and $H_{S2}$. In some implementations, the spacing distance Hs may change in direct correspondence to the intersection angle θ among a plurality of the support surfaces 22 angularly distributed about the camera axis $A_C$. The relationship between the intersection angle θ and the spacing distance Hs may be defined by Equation 2 to maintain a constant intersection distance $D_{int}$. In this configuration, the rotation of the camera apparatus 10 relative to the shaft 24 of the surgical tool 12 may only adjust the perspective of the field of view 32 relative to the working end 34 without varying the central point of intersection or target area 72 of the focal region 30 within the working distance $L_f$ of the camera. Alternatively, in some implementations, it may be beneficial or desirable to vary the intersection distance $D_{int}$ based on the orientation or rotation of the body 18 of the camera apparatus 10 and the corresponding support surface 22 in contact with the shaft 24. In such cases, the spacing distance Hs may be maintained or changed in combination with the intersection angle to shift the intersection distance closer to or further away from the distal end portion 20b of the probe 20 along the camera axis $A_C$. Accordingly, the design of the body 18 of the camera apparatus 10 and the corresponding support surfaces 22 may be adjusted based on this disclosure to allow the camera apparatus 10 to be implemented for a variety of applications and user preferences.

Figure 6C:
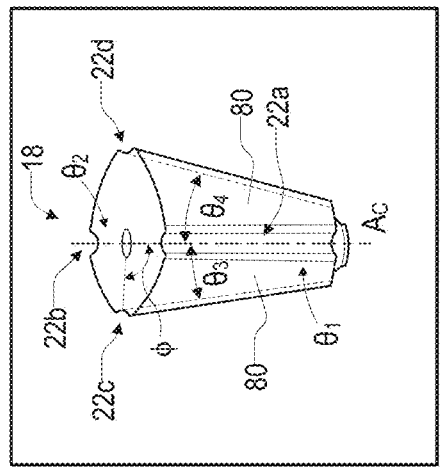
FIG. 6C is a side projected view demonstrating an exemplary implementation of a body of a camera apparatus including a plurality of support surfaces.
Figure 6D:
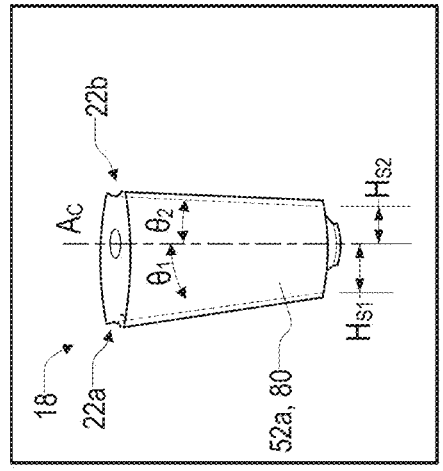
FIG. 6D is a side projected view demonstrating an exemplary implementation of a body of a camera apparatus including a plurality of support surfaces.
Figure 6E:
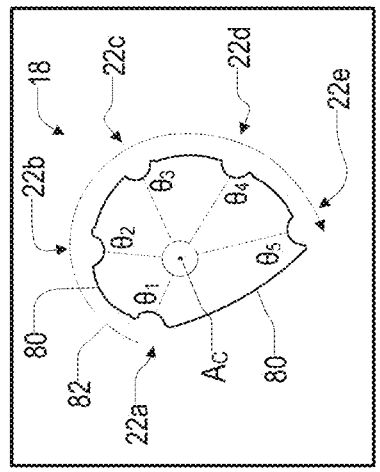
FIG. 6E is a top view demonstrating an exemplary implementation of a body of a camera apparatus including a plurality of support surfaces.

As shown in FIGS. 6C-6E, the number of support surfaces 22 and corresponding geometry of the body 18 formed by the camera apparatus 10 may widely vary depending on the application. As demonstrated in FIG. 6C, the body 18 comprises three support surfaces 22a, 22b, 22c that may be angularly oriented at a spacing angle ϕ about the camera axis $A_C$. As shown, the spacing angle ϕ is constant between each of the support surfaces 22a, 22b, 22c. However, the angular spacing of the support surfaces and the corresponding shape and proportions of the body 18 extending between the support surfaces 22 may vary depending on the application. The intermediate surfaces 80 formed by the body 18 between the support surfaces 22 may correspond to various concave, convex, rounded, segmented, or other surface contours extending between the support surfaces 22. In various implementations, the intermediate surfaces 80 may provide for smooth contours that may allow the shaft 24 of the surgical tool 12 to smoothly slide over the intermediate surfaces 80 before engaging the depression 46 or channel 48 formed by the support surface 22 as a result of the camera apparatus 10 rotating about the camera axis $A_C$.

As shown in FIG. 6D, the support surfaces 22a, 22b, 22c, and 22d are similarly angularly distributed evenly about the camera axis $A_C$ at the spacing angle ϕ. As shown in FIGS. 6C and 6D, each of the intersection angles θ may differ among the support surfaces 22. For example, in FIG. 6C, the second intersection angle $\theta_2$ is greater than the third intersection angle $\theta_3$. Though not shown due to the perspective of FIG. 60, $\theta_1$ may be less than $\theta_2$ or $\theta_3$. As demonstrated in FIG. 6D, each of the intersection angles θ may differ for the corresponding first support surface 22a, second support surface 22b, third support surface 22c, and fourth support surface 22d. In the example shown, the first intersection angle $\theta_1$ may be less than the second intersection angle $\theta_2$. The third intersection angle $\theta_3$ may be greater than the second intersection angle $\theta_2$ and the fourth intersection angle $\theta_4$ may be greater than the third intersection angle $\theta_3$. Though each of the intersection angles θ are described as differing in correspondence to each of the support surfaces 22, one or more of the intersection angles θ may be the same depending on the desired configuration of the camera apparatus 10.

Referring now to FIG. 6E, yet another example of a geometry for the support surfaces 22 of the body 18 is shown from a top view perspective of the body 18 opposite the camera probe 20. In the example shown, the body 18 may comprise five distinct support surfaces 22a-22e distributed at various spacing angles $\phi_1$-$\phi_5$ about the camera axis $A_C$. In this configuration, the body 18 may spiral outward along a spiraled contoured surface 82, thereby gradually increasing a maximum radial spacing of each of the support surfaces 22 about the camera axis $A_C$. The gradual increase in the radial spacing of the support surfaces 22 from the camera axis $A_C$ may provide for a smooth transition from the first support surface 22a to the second support surface 22b, the second support surface 22b to the third support surface 22c, and so on. Between the first support surface 22a and the fifth support surface 22e, a smooth contour may be provided over the intermediate surface 80 allowing the shaft 24 to smoothly slide between each of the support surfaces 22. Though not clearly depicted in FIG. 6E, the gradual increase of the radial spacing of each of the support surfaces 22 from the camera axis $A_C$ may result in the corresponding increases in the intersection angles $\theta_1$-$\theta_5$. In this configuration, the intersection angles $\theta$ associated with each of the support surfaces 22 may gradually increase as the body 18 of the camera apparatus 10 is rotated relative to the shaft 24 of the surgical tool 12. Accordingly, the camera apparatus 10 may be implemented to provide a variety of features that may suit the preferences and/or requirements associated with various surgical procedures.

As previously discussed, the intersection angle $\theta$ corresponding to each of the support surfaces 22 may vary alone or in combination with the spacing distance HS. Referring to FIG. 6E as an example, each of the intersection angles $\theta_1$-$\theta_5$ may change alone or in combination with the corresponding spacing distances $H_{S1}$-$H_{S5}$ (not shown). In various implementations, the intersection angle $\theta$ and spacing distance Hs may change, such that the working distance $L_f$ remains constant as the intersection angle $\theta$ changes. Referring again to Equation 4, the working distance $L_f$ is directly proportional to a relationship between the spacing distance HS and the intersection angle $\theta$ for a given camera apparatus 10. By maintaining or adjusting the features in Equation 4 may, the intersection distance $D_{int}$ may be varied or maintained over a range of intersection angles to $\theta$ suit the desired operation of the camera apparatus 10.

Based on the geometry of the body 18, the spacing distance Hs may be changed in combination with the intersection angle $\theta$ to ensure that the working distance $L_f$ associated with the focal region 30 within the field of view 32 of the camera apparatus 10 is maintained or varies among the support surfaces 22 aligning the shaft 24 of the surgical tool 12. Though maintaining the working distance $L_f$ may be preferred in some implementations, it may also be beneficial to change the working distance $L_f$ among the support surfaces 22, such that the position of the focal region 30 along the tool axis $A_T$ changes with the perspective associated with one or more of the intersection angles $\theta$. Finally, though not denoted in FIG. 6E for clarity, the spacing angles $\phi$ between or among the various support surfaces 22 may vary based on the desired geometry of the body 18 and may be adjusted to ensure that the operation of the camera apparatus 10, particularly the rotational maneuvering among the support surfaces 22 over the intermediate surfaces 80, is optimized for maneuvering by the user during a surgical procedure.

Figure 7:
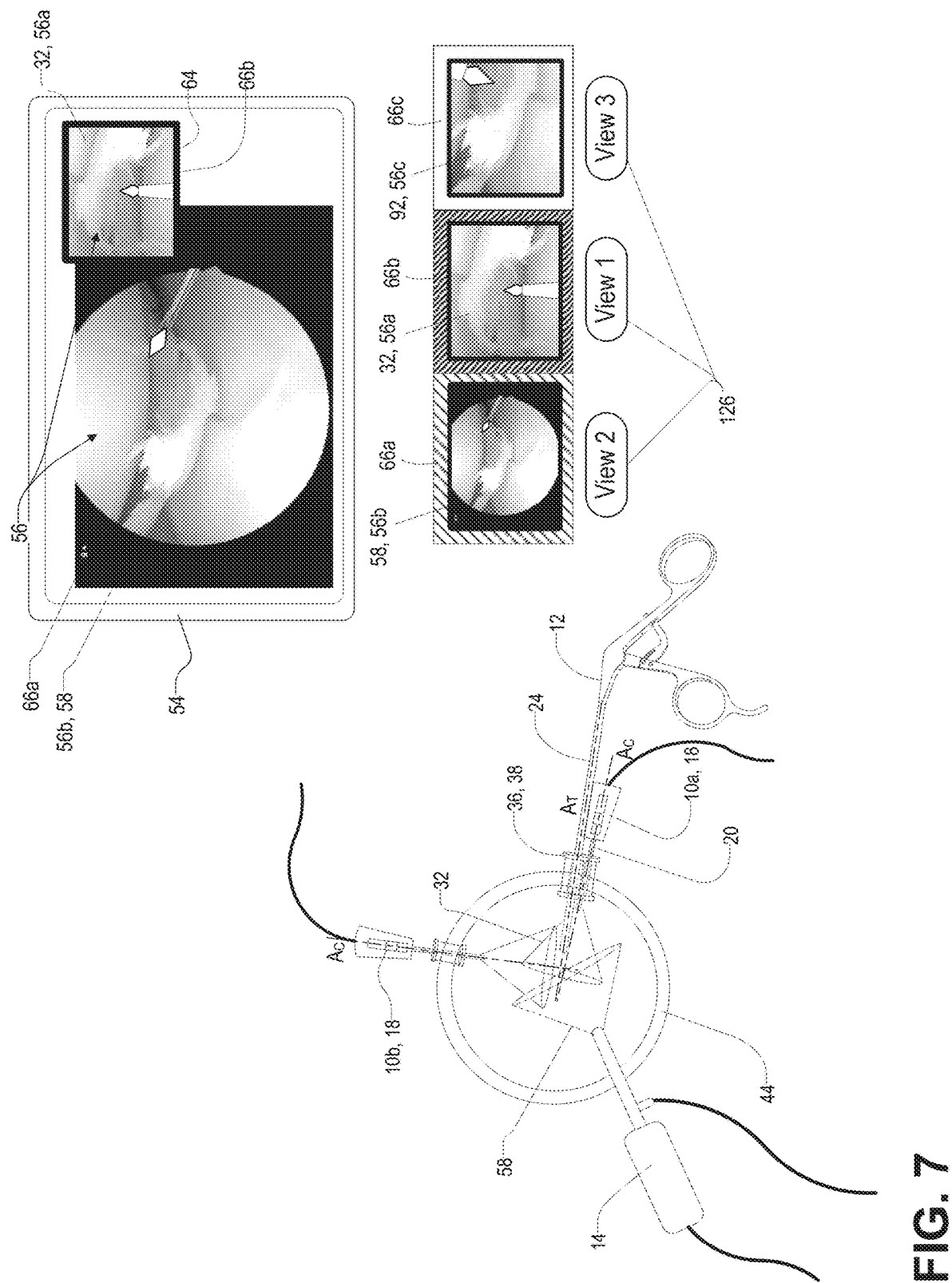
FIG. 7 is an illustrative diagram demonstrating a plurality of compatible devices including one or more cameras that may be tracked within a surgical coordinate system to track relative positions and/or orientations.
Figure 8:
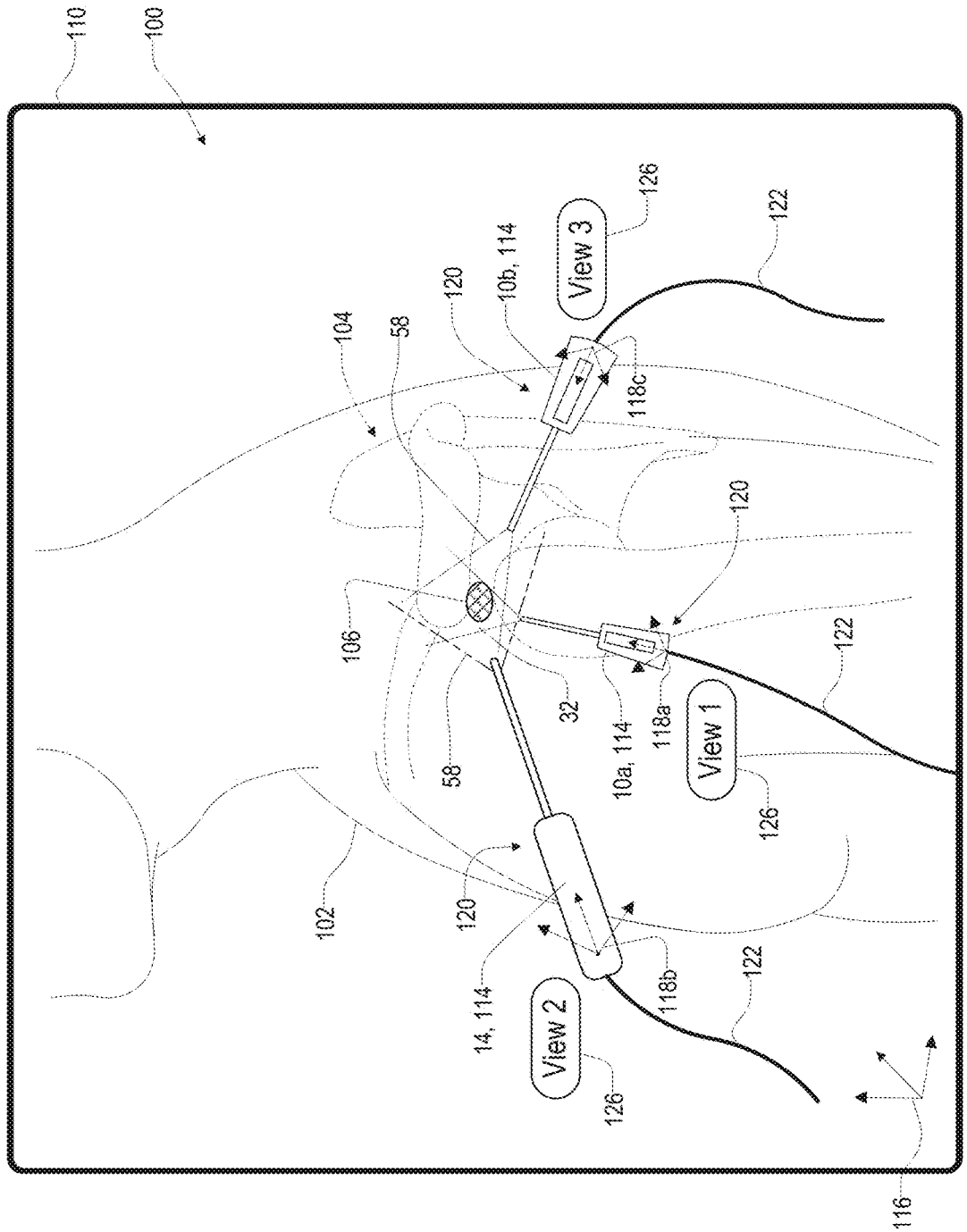
FIG. 8 is a diagram demonstrating a simulated display window generated by an imaging system presenting locations of a plurality of compatible devices in a surgical coordinate system.

Referring now to FIGS. 7 and 8, additional features related to the operation of the imaging system 16 are described. As shown in FIG. 7, in some implementations, the imaging system 16 may be configured to selectively present image data from a plurality of cameras or camera apparatuses 10 at various perspectives 56 having different orientations distributed about the patient cavity 44. As previously introduced, the imaging system 16 may be in communication with various camera apparatuses 10, surgical tools 12, endoscopes 14, or various other surgical devices that may be implemented in combination herewith. For clarity, these devices may generally be referred to as compatible devices 90, each of which may be utilized alone or in combination with the features and operations discussed herein. In the example shown, three separate imaging devices or scopes are utilized in combination, including a first camera apparatus 10a, a second camera apparatus 10b, and the endoscope 14. Like the previously described examples, the first camera apparatus 10a may capture image data from a first perspective 56a, the endoscope 14 may capture image data from the second perspective 56b, and the second camera apparatus 10b may capture image data from a third perspective 56c.

Each of the perspectives 56 are shown in exemplary fields of view, including the first field of view 32, the second field of view 58, and a third field of view 92 associated with the first perspective 56a, the second perspective 56b, and the third perspective 56c, respectively. Due to the complexity of the system 16 and the various perspectives available for demonstration in a first viewing window 66a and a second viewing window 66b, it may be challenging for a user to maintain an awareness of a spatial orientation of each of the perspectives 56 in the corresponding fields of view 32, 58, 92 relative to the anatomy of the patient and the patient cavity 44. As further discussed in reference to FIG. 8, the video controller 60 may track the orientations of each of the compatible devices 90 relative to one another to assist users in maintaining an awareness of the relative spatial orientation and relative position of each of the devices 90 associated with the imaging system 16. Additionally, the orientations and relative positions of the devices 90 in communication with the imaging system 16 may be presented in relation to an anatomical graphic 100 or simulated depiction of an anatomy or region near the patient cavity 44 to demonstrate the relative positions and/or orientations of the devices 90 relative to the graphic 100.

As shown in FIG. 8, graphic representations of each of the exemplary devices 10a, 10b, and 14 are depicted demonstrating the relative positions and spatial orientations of the devices in relation to the anatomical graphic 100. As shown, the anatomical graphic 100 may demonstrate a superficial depiction 102 of the relevant anatomy of the patient and may, in some cases, further demonstrate an internal depiction 104 representing one or more internal anatomical features (e.g., bone, muscle, cartilage, organs, etc.) associated with the relative anatomy of the patient local to the patient cavity 44. In some implementations, the anatomical graphic 100 including the superficial depiction 102 and/or the internal depiction 104, may correspond to graphic representations that may be rendered based on one or more representative or patient-specific scans (e.g., x-rays, ultrasounds, magnetic resonance imaging, computed tomography scans, etc.). In such examples, the anatomical graphic 100 may include one or more specific patient features that may further assist in guiding the surgeon to complete a procedure or identify one or more regions of interest 106 within the patient cavity 44. In this way, the spatial orientations and positions associated with the devices 90 may be demonstrated in relation to the anatomical graphic 100 to assist users of the imaging system 16 to visualize and manipulate the associated tools and equipment to successfully complete various surgical procedures.

As discussed in further detail in reference to FIG. 7, the scan data, graphics, photographs or other related visual representations relevant to the surgical site or patient cavity 44 may be accessed via an external device or server 210 in communication with the system 16. For example, in some cases, the anatomical graphic 100 or similar graphic information may be accessed in a procedure-specific database to provide representative graphics, images, or representative scans relevant to the procedure. The procedure and corresponding graphics, scans, or image data (e.g., 100, 102, 104) may be identified or entered as an initial setup procedure of the imaging system 16 in preparation for a procedure. Based on the type of procedure, the graphic 100 and/or imaging corresponding to the relevant patient anatomy including the superficial depiction and the internal depiction 104 may be loaded to a local memory (e.g., the memory 200) and displayed on the display device 54. In this way, the scans or image data (e.g., 100, 102, 104) may be presented on the display device 54 or various user interfaces (e.g., a tablet, computer console, touchscreen, etc.) to display the optional perspective view 56a, 56b, 56c and corresponding graphic depictions 120 or selectable icons 126 in the corresponding positions and/or orientations of the local coordinate systems 118a, 118b, 118c on the display screen 54. In this way, the controller 60 may provide for the presentation of the graphic depictions 120 or selectable icons 126 of the camera apparatuses 10a, 10b, scope(s) 14, or various other medical device 12 in the corresponding positions and orientations detected by the tracking apparatuses 114 in relation to the corresponding patient anatomy mapped to the surgical coordinate system 116. Such depictions may provide for an intuitive, visually-apparent user interface allowing users to readily identify a desired field of view 32, 58, 92 or corresponding viewing window 66a, 66b, 66c for presentation to assist with the surgical procedure.

Though primarily discussed in reference to the camera apparatuses 10a, 10b, scope(s) 14, etc., the systems and methods described can similarly be applied to present similar positional information and corresponding operating information for various surgical tools 12 that may be in communication with the system 16. For example, an exemplary surgical tool may correspond to a shaver handpiece that may be used in combination with the apparatus 10a and the endoscope 14. In such cases, the surgical tool 12 (e.g., the shaver handpiece) may similarly include one or more tracking apparatuses 114 allowing the corresponding position and orientation to be tracked by the system 16 in the surgical coordinate system 116. The device graphics 120 representative of the surgical tool 12 may similarly be accessed via the external device, server 210, and/or memory to present graphics 120 representing the surgical tool 12 in the viewing window 110 and positioned/oriented in the surgical coordinate system 116 in relation to the corresponding graphics, scans or image data (e.g., 100, 102, 104) as well as the positions/orientations of the camera apparatus (es) 10 and/or endoscopes 14. Examples of surgical tools 12 that may be demonstrated in the viewing window may include but are not limited to various surgical cutting tools (e.g., shavers, rasps, burrs, dissectors, drills, sabers, resectors, blades, etc.) and ablation devices, catheters, pumps, suction or aspiration devices, and similar tools.

Still referring to FIG. 8, the spatial orientation and positions of the devices 90 may be depicted as representative graphics relative to the and anatomical graphic 100 within a viewing window 110. To clearly demonstrate and track the orientations and positions of the compatible devices 90 relative to each other and the anatomy of the patient or the patient cavity 44, the devices 90 may be equipped with one or more tracking apparatuses 114 that may function alone or in combination to monitor and update the relative positions and orientations of the devices 90 within a surgical coordinate system 116. As shown, the orientations and positions of each of the compatible devices 90 are represented by individual local coordinate system 118. For example, a first local coordinate system 118a may define the position and orientation of the first camera apparatus 10a and the corresponding first perspective 56a. Similarly, a second coordinate system 118b may define the orientation and position of the endoscope 14 and the corresponding second field of view 58 within the surgical coordinate system 116. A third local coordinate system 118c may define the relationship of the orientation and position of the second camera apparatus 10b as well. In operation, the controller 60 of the system 16 may track the positions and orientations of each of the local coordinate systems 118 relative to the surgical coordinate system 116 to accurately generate corresponding device graphics 120 illustrating the relative relationship among the compatible devices 90 demonstrated in the viewing window 110.

To accurately track the positions and orientations of the compatible devices 90 to position and update the locations of the local coordinate systems 118, the controller 60 may monitor and maintain communication with a plurality of the corresponding tracking apparatuses 114. For example, in some implementations, the compatible devices 90 may be tethered to a tracking system via a flexible tether 122 that may utilize one or more shape sensors (e.g., strain sensors associated with fiber Bragg gradings) to track the local coordinate systems 118 within the surgical coordinate system 116. In operation, a translational and/or rotational path of the flexible tether 122 may be tracked through the surgical coordinate system 116. For example, the sensor(s) associated with the flexible tether 122 may correspond to fiber Bragg grading sensors or optical sensors extending along the length of the tether 122 that may operate to detect the bending or extent of curvature as well as a direction of curvature based on signals received from the corresponding shape sensors distributed along the length of the tether 122. In this way, the controller 60 may track the local coordinate systems 118 relative to each other in the surgical coordinate system 116. Additionally, one or more flexible tethers 122 may be connected to the anatomy of the patient at a predetermined location, such that changes in the relative location of the patient within the surgical coordinate system 116 may similarly be updated and demonstrated by the anatomical graphic 100. In this way, the local coordinate systems 118 associated with each of the compatible devices 90 may be tracked throughout the operation of the imaging system 16 to inform users of the relative positions of, in this case, the perspectives 56 relative to the patient cavity 44 and/or patient anatomy.

In some implementations, the device graphics 120 may correspond to interactive graphics that may be incorporated on a touchscreen or user interface display that may provide on-screen selections corresponding to selectable view icons 126 in viewing window 110 on the display 54. In this way, a user may interact with a user interface associated with the viewing window 110 shown in FIG. 8 to selectively activate each of the corresponding fields of view 32, 58, 92 for display by the imaging system 16. Additionally, based on the orientation of the devices 90 relative to the patient the patient cavity 44 and/or patient anatomy, the controller 60 may be configured to label the corresponding views and/or the associated view icons 126 with the anatomical location of the views relative to the patient anatomy. For example, in various examples, it may be beneficial to identify the location and orientation of the views associated with each of the perspectives 56 in anatomical terms that may be identified based on the relative position and orientation of the local coordinate systems 118 relative to the surgical coordinate system 116 and/or the anatomy of the patient. In this configuration, the views may be described in anatomical terms (e.g., anterior, mid-lateral, posterior, etc.), such the corresponding views may be demonstrated in space, labeled based on the anatomical posture, and recorded and tracked for diagnostic purposes.

In various implementations, the tracking apparatus 114 or apparatuses 114 associated with the monitoring of each of the local coordinate systems 118 of the compatible devices 90 may be implemented as multiple one or more tracking technologies that may be used alone or in combination. For example, in addition to or as an alternative to the flexible tethers 122, the position of each of the local coordinate systems 118 of the compatible devices 90 may be tracked via one or more wireless triangulation, Time of Flight (ToF), and/or Angle of Arrival (AoA) detection methods or similar technologies provided via a wireless communication interface (e.g., Zigbee, Ultra-Wide Band, radio frequency, infrared, Bluetooth low energy, near-field communication, etc.). Such detection and tracking may provide for the relative positions of the local coordinate system 118 within the surgical coordinate system 116. Additionally, the orientation of each of the local coordinate systems 118 may be tracked by one or more attached or incorporated orientation sensors, which may be in the form of one or more inertial or directional sensors (e.g., accelerometers, gyroscopes, magnetometers, etc.). The operation of the orientation sensors may provide for indications of orientations of each of the compatible devices 90 in a global coordinate system which may be aligned with the surgical coordinate system 116. In this way, the combination of one or more inertial measurements combined with one or more wireless radio frequency location tracking methods may be processed and utilized by the video controller 60 to monitor the relative positions and orientations of the local coordinate systems 118 to generate the device graphics 120 similar to those shown in FIG. 8. Though specific technologies are described in reference to tracking apparatuses 114, it shall be understood that similar tracking technologies may be implemented including, but not limited to, image or video-based object tracking, stereoscopic tracking (e.g., computer vision), strain gauges or strain arrays, or similar technologies.

Figure 9:
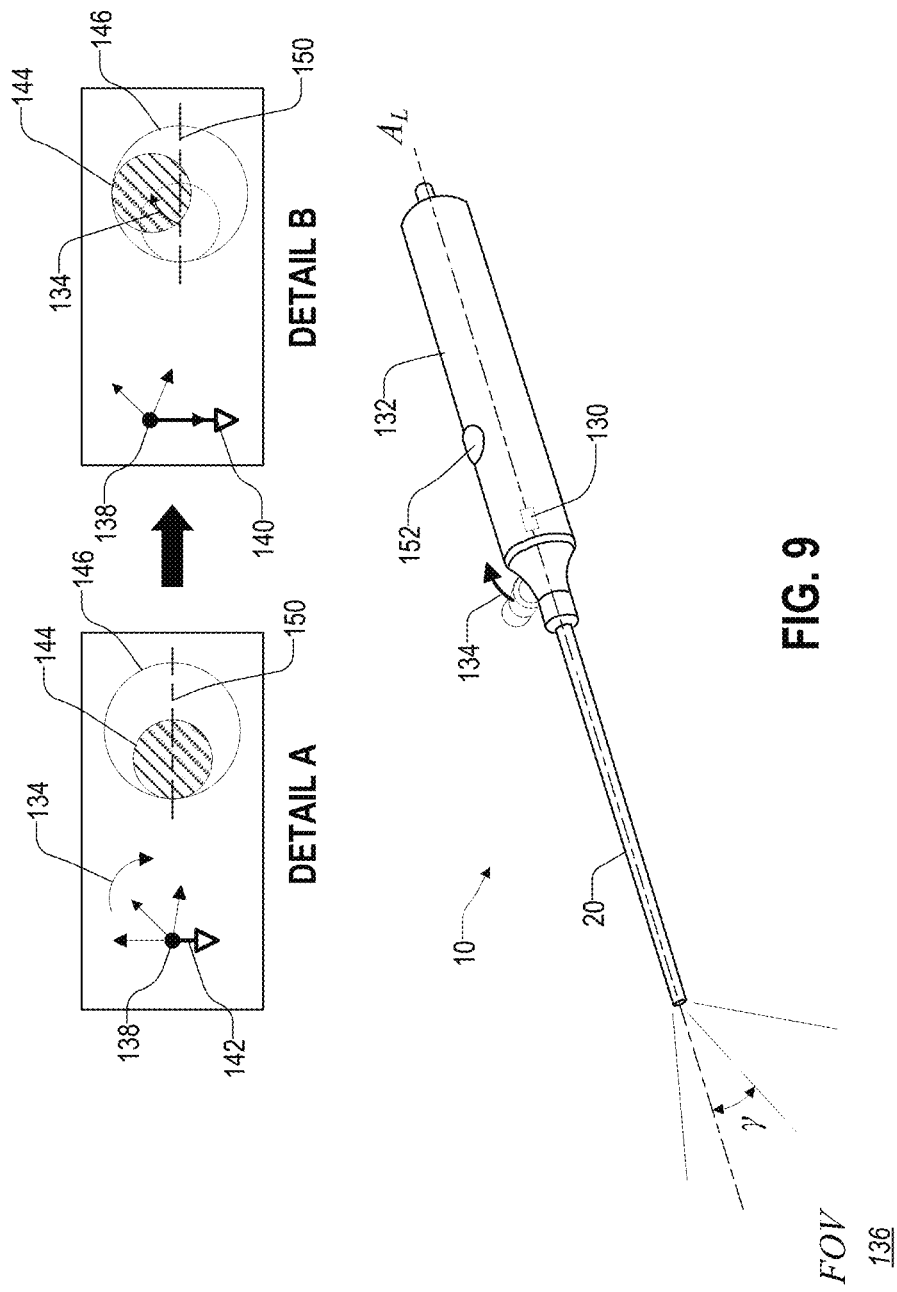
FIG. 9 is an illustrative projected view of a surgical camera apparatus demonstrating the operation of a camera orientation sensor.
Figure 10C:
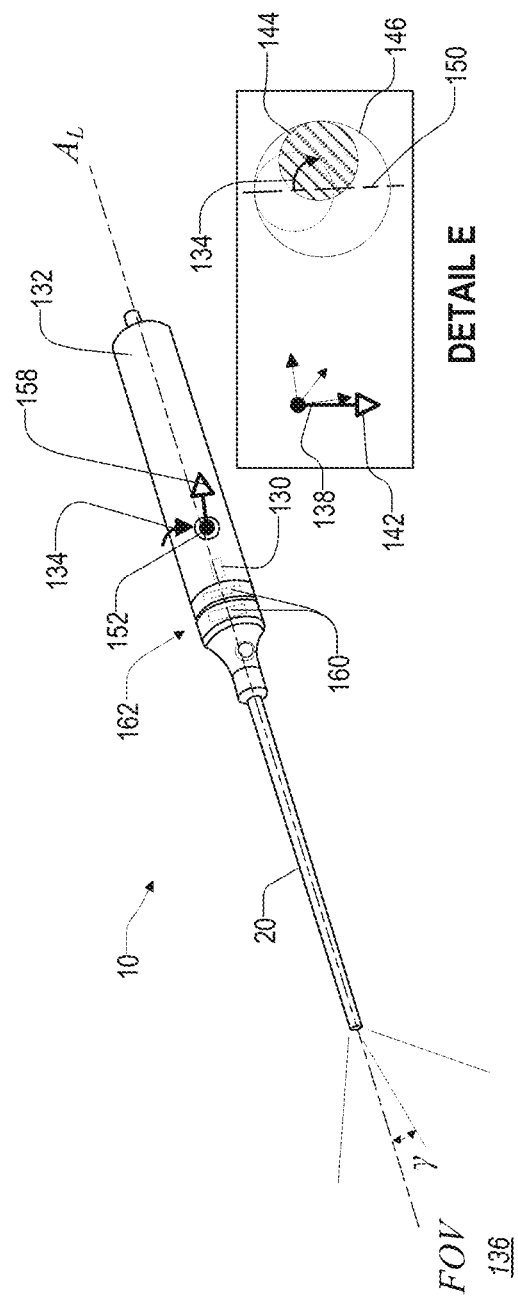
FIG. 10C is an illustrative projected view of a camera apparatus demonstrating a second camera orientation and the second scope orientation.
Figure 11:
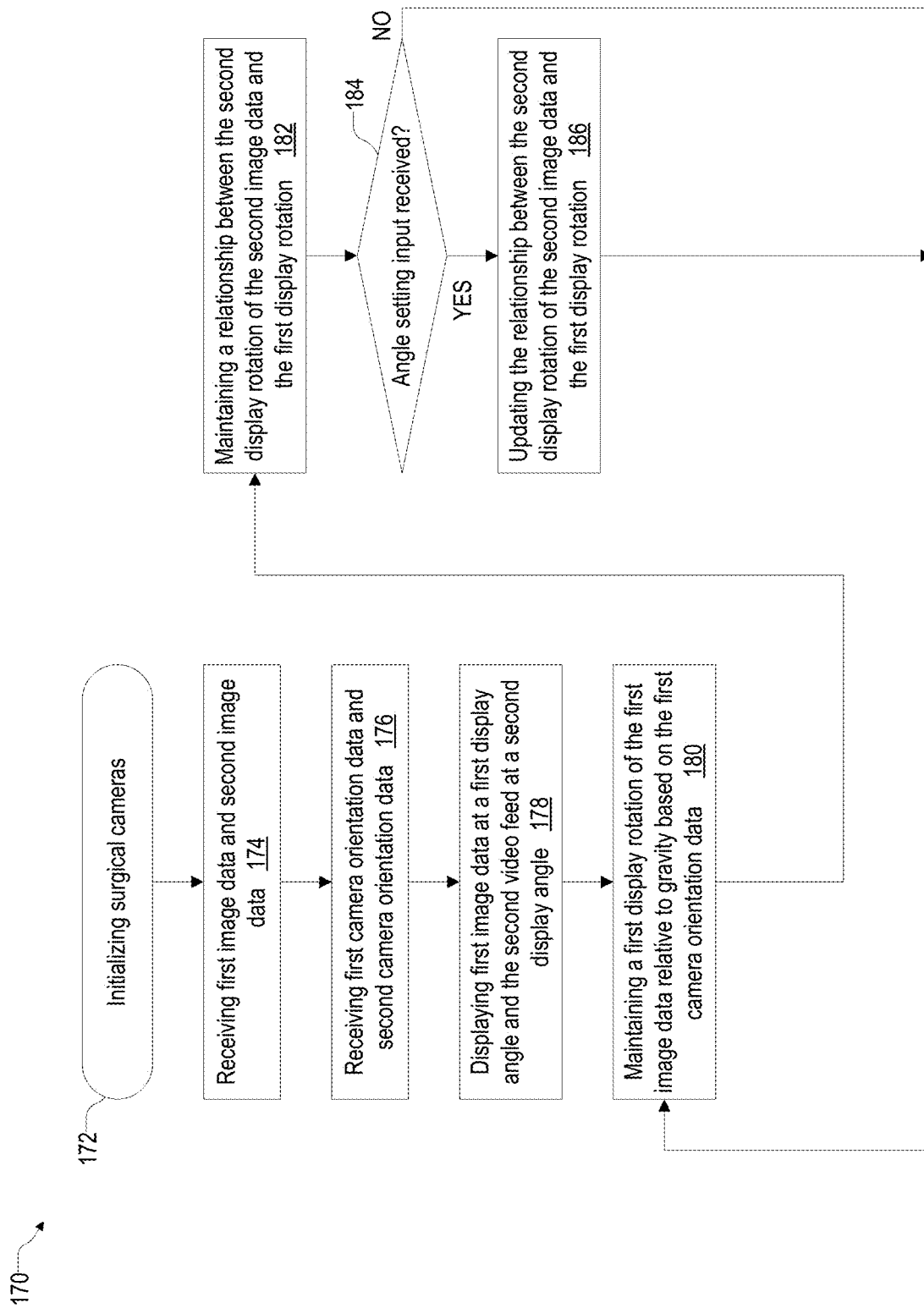
FIG. 11 is a flowchart demonstrating a method for displaying a plurality of video feeds from a plurality of surgical cameras.

Referring now to FIGS. 9-11, various examples of the camera apparatus 10 are described in reference to the coordinated presentation of multiple image feeds presented on the display 54 of the imaging system 16. As demonstrated in FIG. 9, the camera apparatus 10 may include a first tracking apparatus 114 in the form of a camera orientation sensor 130, which may be disposed within or otherwise in connection with a camera body 132 or handle body of the camera apparatus 10. In operation, the camera orientation sensor 130 may detect the orientation of the camera body 132 in connection with the probe 20 or scope extending from the camera body 132 along a longitudinal axis $A_L$. In this configuration, the camera orientation sensor 130 may detect the orientation of the camera body 132 and the scope or probe 20 relative to a fixed bearing or direction (e.g., gravity).

As shown in FIG. 9, an arrow 134 represents a rotation of the camera body 132 as detected by the camera orientation sensor 130. In operation, the controller 60 may receive image data from the camera apparatus 10 demonstrating a field of view 136 as well as orientation data from the camera orientation sensor 130 indicating the spatial orientation of the camera apparatus 10. For reference, Details A and B demonstrate a coordinate system 138 of the camera apparatus 10 is relative to a gravity vector 142 illustrating the spatial orientation. Additionally, a rotational position 144 of the field of view 136 is shown relative to a rotational range 146. The rotational range represents range of the position 144 of the field of view 136 when rotated about the longitudinal axis $A_L$. As shown in Details A and B, the rotation associated with the arrow 134 may result in an exemplary rotation of the camera apparatus 10 about the longitudinal axis $A_L$ of approximately 90°. Corresponding to the rotation about the longitudinal axis, the coordinate system 138 rotates 90° relative to the gravity vector 142 and about the longitudinal axis $A_L$. The rotation of the camera apparatus 10 about the longitudinal axis $A_L$ may result in a change in the rotational position 144 of the field of view 136 within the rotational range 146 caused by the angular offset of a scope angle $\rho$ relative to the longitudinal axis $A_L$.

In response to detecting the rotation of the camera apparatus 10, the controller 60 may be configured to rotationally offset the image data presented in the field of view 136, such that the objects and/or features maintain a fixed rotational relationship to a horizon 150, which may be defined as perpendicular to the gravity vector 142. As shown in Details A and B, the rotational position 144 of the field of view 136 may change within the rotational range 146. However, in response to the change in the direction of the gravity vector 142 and corresponding rotation of the camera apparatus 10, the image data presented on the display 54 may be rotated, such that the relationships of objects depicted in the field of view 136 are maintained relative to the horizon 150. Such operation of the camera apparatus 10 may be referred to as "horizon control."

When applied to a plurality of camera apparatuses 10 or imaging devices as previously discussed in reference to FIGS. 7 and 8, the adjustment of the image data presented on the display 54 in consistent orientation relative to the horizon 150 may ensure that features captured in the fields of view (e.g., the first field of view 32, second field of view 58, etc.) may be presented on the display 54 in a consistent orientation and relationship relative to the horizon 150. Additionally, in some implementations, one or more of the fields of view 32, 58, 92, etc. may be maintained at a fixed or user-selected angular relationship relative to the horizon 150 or gravity vector 142. For example, the first camera apparatus 10*a* may be presented with the corresponding image data in the field of view 32 aligned in a first orientation relative to the gravity vector 142 while the image data captured by the second camera apparatus 10*b* may be presented in a second consistent or fixed relationship relative to the gravity vector 142. As shown in FIG. 9, the relationship of the rotation of the field of view 136 relative to the gravity vector 142 may be optionally selected via a user input 152, which may be incorporated on the camera body 132 or otherwise in communication with the camera apparatus 10.

Referring now to FIGS. 10A, 10B, and 10C, an exemplary implementation of the camera apparatus 10 is shown including the camera orientation sensor 130 and a scope orientation sensor 160. In the example shown in FIG. 10, the camera orientation sensor 130 may be in connection with the camera body 132 or the scope or probe 20 of the camera apparatus. The probe 20 or scope may be in connection with the camera body 132 via a rotational coupling 162. The scope or probe 20 may be free to rotate about the longitudinal axis $A_L$ relative to the camera body 132. The scope orientation sensor 160 may correspond to a rotation sensor (e.g., a potentiometer, encoder, etc.) and may output a rotation signal indicative of a rotational relationship between the camera body 132 and the probe or scope 20 about the longitudinal axis $A_L$. Accordingly, based on the camera orientation data supplied by the camera orientation sensor 130 and the scope orientation data supplied by the scope orientation sensor 160, the camera apparatus 10 may provide a variety of control features similar to the control relative to the horizon 150 as previously described.

Referring first to FIG. 10, the camera body 132 is shown with the user input 152 oriented in an upward direction 164, generally opposite the gravity vector 142. In response to a rotation of the scope or probe 20 about the longitudinal axis $A_L$ relative to the camera body 132, the controller 60 may detect a change in a rotation angle ρ of the scope or probe 20 relative to the camera body 132 as reported by the scope orientation sensor 160. As demonstrated in Details C and D, the rotational position 144 of the field of view 136 may change within the rotational range 146 as a result of the rotation of the scope or probe 20 via the rotational coupling 162. However, the camera orientation data recorded by the camera orientation sensor 130 may continue to report that the gravity vector 142 remains constant as illustrated in reference to the coordinate system 138. In response to the corresponding change in the scope orientation data relative to the camera orientation data reported by the camera orientation sensor 130, the controller 60 may update or rotate the image frames associated with the image feed provided by the camera apparatus 10 to counteract the apparent change in the rotation angle ρ of the scope 20 or probe. In this way, the objects or features presented in the field of view 136 may maintain a constant relationship relative to the horizon 150 as demonstrated in Details C and D.

As shown in FIG. 10C, the controller 60 may also detect changes in the camera orientation data as reported by the camera orientation sensor 130. As illustrated by comparing FIGS. 10B and 10C, the camera apparatus 10, including the camera body 132 and the probe or scope 20, are rotated together approximately 90° about the longitudinal axis $A_L$. As shown relative to the coordinate system 138, the controller 60 may detect the change in direction of the gravity vector 142 shown in Detail E based on the camera orientation data communicated by the camera orientation sensor 130. In response to the change in the direction of the gravity vector 142 relative to the coordinate system 138, without a change in the scope orientation data as reported by the scope orientation sensor 160, the controller 60 may allow the orientation of the horizon 150 to rotate about the longitudinal axis $A_L$ in conjunction with the change of the rotational position 144 of the field of view 136. As a result, the image data presented in the field of view 136 on the display 54 may shift in position and orientation relative to the gravity vector 142. Accordingly, the controller 60 may selectively apply the horizon correction or rotation of the image data responsive to a detected change in the direction of the gravity vector 142 and/or in the rotation angle ρ of the scope or probe 20 relative to the camera body 132.

As demonstrated in FIGS. 10A, 10B, and 10C, the rotational position 144 of the field of view 136 may be changed by adjusting the rotation angle ρ at the rotational coupling 162 while maintaining a relationship to the horizon 150. Alternatively, the camera apparatus 10 may be rotated without changing the rotation angle ρ, which may result in a change in the horizon 150 relative to the gravity vector 142 and corresponding changes presented in the image data of the field of view 136 presented on the display 54. Additionally, similar to the camera apparatus 10 discussed in reference to FIG. 9, receipt of an input to the user interface 152 may update an offset of the horizon 150 relative to the coordinate system 138. In this way, the combined operation of the camera orientation sensor 130 and the scope orientation sensor 160 may provide for improved flexibility in operation of the camera apparatus 10 individually or in a system with multiple imaging devices or camera apparatuses.

As discussed herein, the camera orientation sensor 130 may correspond to various devices that may detect the orientation of the camera apparatus 10 relative to gravity, a geomagnetic field, or similar forces. For example, in various implementations, the camera orientation sensor 130 may be implemented as one or more of a gyroscope, an accelerometer, a magnetometer, and/or an inertial measurement unit (IMU). As previously discussed, the scope orientation sensor 160 may correspond to an encoder, a potentiometer, or similar angular rotation sensors. In some implementations, the scope orientation sensor 160 may be implemented as an accelerometer, gyroscope, IMU, or similar devices. In such implementations, the scope orientation data reported by the scope orientation sensor 160 may be interpreted by the controller 60 relative to the camera orientation data reported by the camera orientation sensor 130. Accordingly, the orientation sensors 130, 160 may be flexibly implemented and incorporated in one or more of the probe or scope 20 and/or the camera body 132 to provide for the functionality discussed herein.

Referring now to FIG. 11, a flowchart is shown demonstrating a method 170 for displaying image data from a plurality of surgical cameras, such as the camera apparatus 10. In operation, the method 170 may be applied by the controller 60 and may begin in response to receiving first image data and second image data from first and second camera apparatuses 10a, 10b (174). Additionally, concurrent with or in rapid succession with the receipt of the image data, the controller 60 may receive first camera orientation data from the first camera apparatus 10a and second camera orientation data from the second camera apparatus 10b (176). As discussed in reference to FIGS. 9 and 10, the camera orientation data may correspond to information captured by one or more of the camera orientation sensor 130, the scope orientations sensor 160, or, more generally, by one or more of the tracking apparatuses 114. In this way, as demonstrated in step 178, the controller 60 may display the first image data at a first display angle and the second image data at a second display angle, one or more of which may be maintained or offset relative to the gravity vector 142.

With the image data from the camera apparatuses 10a and 10b, as well as the corresponding orientation data, the controller 60 may receive video streams including the first image data and the second image data. In the example shown, the controller 60 may adjust a first video feed of the first image data relative to the gravity vector 142 in response to changes in the orientation data communicated by one or more of the camera orientation sensor 130, the scope orientation sensor 160, and/or the orientation and position data communicated by the tracking apparatuses 114 (180). Further, the controller may adjust an orientation or position of second video feed from the second image data based on a relationship between the orientation data of the second camera apparatus 10b (182). The orientation of the second image data may be adjusted based on the direction of the gravity vector 142 or relative to the first camera apparatus 10a. In this way, the controller 60 may independently control the orientation and/or position of a plurality of video feeds from the plurality of camera apparatuses 10a, 10b.

In general, the controller 60 may adjust the first and second image data such that each of the corresponding video feeds maintains a rotational orientation relative to the gravity vector 142. In this way, the image data presented as parallel video feeds on the display 54 may be presented with consistent orientations relative to the gravity vector 142 or the horizon 150. Additionally, in some implementations, the second image data may be maintained at a fixed rotational relationship or user-selected angular offset from the first image data and/or relative to the gravity vector 142 or the horizon 150. In such cases, the orientation data reported by each of the camera apparatuses 10a, 10b may be interpreted by the controller 60 to adjust the image data in direct correspondence to an offset relative to the gravity vector 142 or similarly the horizon 150. Optionally, the second image data captured by the second camera apparatus 10b may be offset by a fixed or user-defined angle relative to the rotational position 144 or rotational angle ρ of the first image data captured by the first camera apparatus 10a. In this way, each of the camera apparatuses 10a, 10b may capture and present image data in a variety of fixed or adjustable relationships relative to the gravity vector 142 or the horizon 150. Though specifically discussed in reference to the first and second image data, it shall be understood that third, fourth, or additional video feeds may similarly be controlled and presented in concurrently or selectively with similar relative or absolute angular or positional adjustments responsive to the data from the sensors 114, 130, 160.

In some implementations, the angular offset between the first camera apparatus 10a or the second camera apparatus 10b relative to the gravity vector 142 or the camera orientation data may be set or adjusted in response to an input to the user interface 152 (184). In response to the angle setting input in step 184 to the user interface 152, the controller 60 may update the relationship between a second display rotation of the second image data and a first display rotation of the first image data (186). Once updated, the angular offset between the sets of images captured by the first camera apparatus 10a and the second camera apparatus 10b may be consistently displayed relative to the offset and relative to the horizon 150. Additionally, the image data captured by each of the camera apparatuses 10 may be independently or relatively displayed in response to changes in the orientation data captured by the orientation sensors 114, 130, 160, etc.

Figure 12:
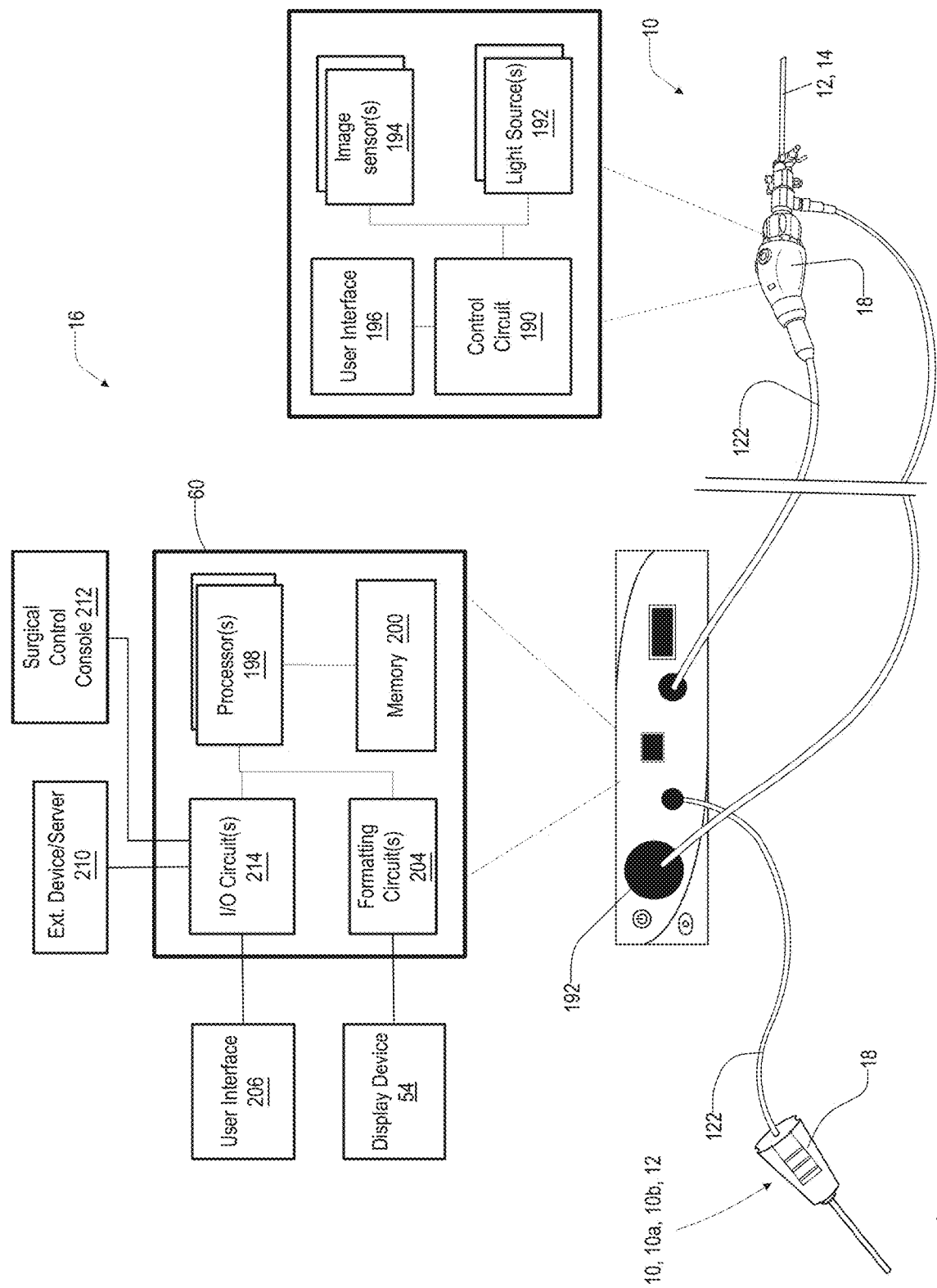
FIG. 12 is a schematic block diagram of a surgical imaging system in accordance with the disclosure.

Referring now to FIG. 12, a block diagram of the imaging system 16 is shown. As discussed throughout the disclosure, the system 16 may comprise the imaging or camera devices 10a, 10b, 14 and may be in communication with various surgical tools 12 via the controller 60. The devices 10a, 10b, 14 may comprise one or more light sources 192, the image sensors 194, and a user interface 196. In various implementations, the devices 10, 14 may correspond to an endoscope, laparoscope, arthroscope, etc. with the elongated probe 20 comprising a narrow distal end suited to various noninvasive surgical techniques. For example, the distal end may include a diameter of less than 2 mm. As demonstrated, the device 10, 14 may be in communication with the controller 60 via communication interface. Though shown connected via a conductive connection, the communication interface may correspond to a wireless communication interface operating via one or more wireless communication protocols (e.g., Wi-Fi, 802.11 b/g/n, etc.).

The light source 192 may correspond to various light emitters configured to generate light in the visible range and/or the near infrared range. In various implementations, the light source 192 may include light emitting diodes (LEDs), laser diodes, or other lighting technologies. The image sensor(s) 194 may correspond to various sensors and configurations comprising, for example, charge-coupled devices (CCD) sensors, complementary metal-oxide semiconductor (CMOS) sensors, or similar sensor technologies.

In various implementations, one or more of the imaging devices (e.g., the endoscope 14) may comprise one or more control circuits 190 configured to control the operation of image sensor(s) 194 and the light source 192 as well as process and/or communicate the image data to the controller 60 or system controller. Additionally, the control circuit 190 may be in communication with a user interface 196, which may include one or more input devices, indicators, displays, etc. The user interface 196 may provide for the control of the imaging device 10 including the activation of one or more routines as discussed herein. The user interface may provide for the selection or toggling of one or more of the image feeds associated with the operation of the camera apparatuses 10 and/or the endoscope 14. The control circuit 190 may be implemented by various forms of controllers, microcontrollers, application-specific integrated controllers (ASICs), and/or various control circuits or combinations.

The controller 60 or system controller may comprise a processor 198 and a memory 200. The processor 198 may include one or more digital processing devices including, for example, a central processing unit (CPU) with one or more processing cores, a graphics processing unit (GPU), digital signal processors (DSPs), field programmable gate arrays (FPGAs), application specific integrated circuits (ASICs) and the like. In some configurations multiple processing devices are combined into a System on a Chip (SoC) configuration while in other configurations the processing devices may correspond to discrete components. In operation, the processor 198 executes program instructions stored in the memory 200 to perform the operations described herein.

The memory 200 may comprise one or more data storage devices including, for example, magnetic or solid-state drives and random access memory (RAM) devices that store digital data. The memory 200 may include one or more stored program instructions, object detection templates, image processing algorithms, etc. The memory 200 may include one or more object tracking routines and corresponding graphic generating routines that may be implemented to operate in coordination with the tracking apparatuses 114 to monitor the positions and spatial orientations of the local coordinate systems 118. Such routines may include instructions to process the associated tracking information and generate the associated device graphics 120 and/or the anatomical graphics 100 and output such information in the viewing window 110 on the display 54.

As previously discussed, in some implementations, the controller 60 may correspond to a display or video controller. In such applications, the controller 60 may include one or more formatting circuits 204, which may process the image data received from the imaging device 10, communicate with the processor 198, and process the image data according to one or more of the operating methods discussed herein. The formatting circuits 204 may include one or more signal processing circuits, analog-to-digital converters, digital-to-analog converters, etc. The display controller may comprise a user interface 206, which may be in the form of an integrated interface (e.g., a touchscreen, input buttons, an electronic display, etc.) or may be implemented by one or more connected input devices (e.g., a tablet) or peripheral devices (e.g., keyboard, mouse, foot pedal, etc.).

As shown, the controller 60 is also in communication with an external device or server 210, which may correspond to a network, local or cloud-based server, device hub, central controller, or various devices that may be in communication with the controller 60 and, more generally, the imaging system 16 via one or more wired (e.g., serial, Universal Serial Bus (USB), Universal Asynchronous Receiver/Transmitter (UART), etc.) and/or wireless communication interfaces (e.g., a ZigBee, an Ultra-Wide Band (UWB), Radio Frequency Identification (RFID), infrared, Bluetooth®, Bluetooth® Low Energy (BLE), Near Field Communication (NFC), etc.) or similar communication standards or methods. For example, the controller 60 may receive updates to the various modules and routines as well as communicate sample image data from the imaging device 10 to a remote server for improved operation, diagnostics, and updates to the imaging system 16. The user interface 196, the external server 210, and/or a surgical control console 212 may be in communication with the controller 60 via one or more I/O circuits 214. The I/O circuits 214 may support various communication protocols including, but not limited to, Ethernet/IP, TCP/IP, Universal Serial Bus, Profibus, Profinet, Modbus, serial communications, etc.

According to some aspects of the disclosure, a camera apparatus for operation in coordination with a surgical tool comprises a tool shaft. The camera apparatus includes a body comprising at least one angled support surface defining an intersection angle; a camera probe having a probe length (LP) in connection with the body at a proximal end portion and extending to a distal end portion, the proximal end portion spaced from the support surface by a spacing distance (Hs) formed by a connection between the body and the support surface; and an optic element of a camera defining a field of view in connection with the distal end portion, wherein the support surface receives the tool shaft and aligns the field of view with the tool axis at a working distance of the camera.

According to various aspects, the disclosure may implement one or more of the following features or configurations in various combinations:
  the body forms a sheath in connection with a perimeter wall of the camera probe;
  the body forms at least one wing extending at the intersection angle from the sheath;
  the at least one wing comprises a plurality of wings extending outward from the body and forming a plurality of angled support surfaces;
  the at least one angled support surface comprises a first angled support surface and a second angle support surface;
  the first angled support surface forms a first intersection angle and the second angled support surface forms a second intersection angle;
  the first angled support surface has a first spacing distance (Hs1) and the second angled support surface has a second spacing distance (Hs2) relative to a probe axis of the camera probe;
  the support surface forms a channel that receives and aligns the tool shaft with the intersection angle;
  the intersection angle defines an intersection between a camera axis extending along at least a portion of the camera probe and a working axis extending along at least a portion of the tool shaft;
  the working axis extends from the tool shaft to a working end or actuator of the surgical tool in connection with the tool shaft; and/or
  the at least one support surface comprises a plurality of angled support surfaces, each having the intersection angle with a different magnitude.

According to another aspect of the disclosure, a camera apparatus for operation in coordination with a surgical tool comprises a tool shaft. The camera apparatus includes a body comprising at least one angled support surface defining an intersection angle; a camera probe having a probe length (Lp) in connection with the body at a proximal end portion and extending to a distal end portion, the proximal end portion spaced from the support surface by a spacing distance (Hs) formed by a connection between the body and the support surface; and an optic element in connection with the distal end portion of the camera probe and defining a field of view having a camera axis or focal axis, wherein the support surface receives the tool shaft and aligns the field of view with the tool axis at a working distance of the camera, wherein the camera probe is retained in contact with the tool shaft by a collar extending about the tool shaft and at least a portion of the camera apparatus.

According to various aspects, the disclosure may implement one or more of the following features or configurations in various combinations:
  the collar forms a portion of a cannula through which the camera probe and the tool shaft extend in an operating configuration;
  the collar is formed of a deformable or elastic material (e.g., polymer, silicon, etc.) that maintains the tool shaft in connection with the angle support surface;
  the cannula comprises at least one lumen that receives the tool shaft and the camera shaft, wherein a perimeter wall of the at least one lumen is enclosed about the tool shaft and the camera shaft and retains the tool shaft in connection with the angled support;
  the at least one lumen comprises a first lumen that receives the tool shaft and a second lumen that receives the camera probe and the perimeter wall is formed by a body of the cannula forming the first lumen and the second lumen;
  the at least one lumen comprises a first lumen that receives the tool shaft and a second lumen that receives the camera probe and the perimeter wall is formed by a body of the cannula forming the first lumen and the second lumen;
  the angled support surface engages the tool shaft and defines the spacing distance between the camera probe and the tool shaft; and/or
  the body forms an enclosure or housing in connection with the camera probe and forming the intersection angle relative to the camera axis.

According to yet another aspect of the disclosure, a camera apparatus for operation in coordination with a surgical tool comprises a tool shaft. The camera apparatus includes a body comprising at least one support surface defining an intersection angle; a camera probe having a probe length (LP) in connection with the body at a proximal end portion and extending to a distal end portion, the proximal end portion spaced from the support surface by a spacing distance (Hs) formed by a connection between the body and the support surface; and an optic element in connection with the distal end portion of the camera probe and defining a field of view having a camera axis or focal axis, wherein the support surface receives the tool shaft and aligns the field of view with a tool axis of the surgical tool at a working distance of the camera, wherein the intersection angle defines an intersection between the camera axis extending along at least a portion of the camera probe and the tool axis extending along at least a portion of the tool shaft.

According to various aspects, the disclosure may implement one or more of the following features or configurations in various combinations:

- the camera probe extends to a probe length from the body and the probe length is defined by the spacing distance (HS) divided by a tangent of the intersection angle minus a working distance (Lf) of the field of view of the camera apparatus;
- the working distance (Lf) is defined as an intersection between the camera axis and the tool axis;
- the probe length (LP) is defined based on the intersection angle;
- the probe length (LP) is less than an intersection distance Dint of the camera axis and the tool axis at the intersection angle;
- the probe length is less than the intersection distance Dint by the working distance (Lf) of the camera;
- the at least one support surface comprises a first angled support surface having a first intersection angle and a first spacing and a second angled surface having a second intersection angle and a second spacing support surface;
- the first intersection angle and the first spacing define a first working length of the field of view along the camera axis and the second intersection angle and the second spacing define a second working length of the field of view along the camera axis;
- the first intersection angle is different from the second intersection angle and the first spacing is different than the second spacing; and/or
- the camera axis and the tool axis intersect at an intersection distance Dint at each of the first intersection angle and the second intersection angle, wherein the intersection distance remains constant for the first support surface and the second support surface.

According to a further aspect of the disclosure, an imaging system comprises a plurality of surgical implements comprising surgical tools and/or camera apparatuses; a plurality of tracking apparatuses in connection with the plurality of surgical implements; and a controller. The controller is configured to track at least one of an orientation and a position of the surgical implements in a surgical coordinate system; generate a graphic representation of the surgical implements based on the orientation and the position; and in response to a selection of the graphic representation of the surgical implements or an associated icon, control an output associated with a selected implement of the surgical implements.

According to various aspects, the disclosure may implement one or more of the following features or configurations in various combinations:

- the output associated with a selected implement of the surgical implements comprises an instruction to display an image feed associated with a first camera of the camera apparatuses;
- the output associated with a selected implement of the surgical implements comprises an instruction to display an image feed associated with a second camera of the camera apparatuses;
- the controller is configured to generate an anatomical graphic depicting a portion of an anatomical feature in the surgical coordinate system relative to the plurality of surgical implements;
- the plurality of tracking apparatuses comprise a patient sensor configured to monitor an orientation and position of the anatomical feature of a patient; and/or
- the tracking apparatuses comprise at least one of a radio frequency communication interface, a computer vision system, and a flexible tether configured to track the relative location and orientation of the surgical implements in the surgical coordinate system.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents

The invention claimed is:

1. A surgical imaging system comprising:
   at least one camera apparatus comprising:
   a camera body comprising an image sensor configured to capture image data in a field of view;
   a scope extending along a longitudinal axis and in connection with the camera body;
   a camera orientation sensor in connection with the camera apparatus, wherein the camera orientation sensor is configured to detect a camera orientation of the camera apparatus;
   a scope orientation sensor configured to detect a scope orientation of the scope relative to the camera body; and
   a controller configured to:
   monitor the camera orientation and the scope orientation; and
   update a rotation of the field of view of the image data in response to a change in the scope orientation relative to the camera orientation.

2. The imaging system according to claim 1, further comprising a user interface, wherein the controller is further configured to:
   offset a horizon direction of the camera apparatus with respect to gravity in response to an input to the user interface.

3. The imaging system according to claim 1, wherein the user interface is in connection with the camera body.

4. The imaging system according to claim 1, wherein the scope orientation sensor is a relative orientation sensor that measures a scope angle of a rotation of the scope about the longitudinal axis relative to the camera body.

5. The imaging system according to claim 1, wherein the scope orientation sensor comprises at least one of an encoder, a potentiometer, a magnetometer, an inclinometer, and an accelerometer.

6. The imaging system according to claim 1, wherein the camera orientation sensor detects an orientation of at least one of the camera body and the scope relative to gravity.

7. The imaging system according to claim 1, wherein the camera orientation sensor comprises at least one of a gyroscope, an accelerometer, a magnetometer, and an inertial measurement unit.

8. The imaging system according to claim 1, wherein the at least one camera apparatus comprises a first camera apparatus and a second camera apparatus, each comprising the camera orientation sensor.

9. The imaging system according to claim 8, wherein the controller is further configured to:
receive first image data from the image sensor of the first camera as second image data from the image sensor of the second camera; and
receive first camera orientation data from the camera orientation sensor of the first camera and second camera orientation data from the camera orientation sensor of the second camera.

10. The imaging system according to claim 9, wherein the controller is further configured to:
adjust a first display rotation of the first image data in conjunction with a second display rotation of the second image data in response to the first camera orientation data and the second camera orientation data.

11. The imaging system according to claim 10, wherein the controller is further configured to:
maintain a rotational relationship between the first display rotation and the second display rotation in response to the first camera orientation data and the second camera orientation data.

12. The imaging system according to claim 11, wherein the controller is further configured to:
update the rotational relationship between the first display rotation and the second display rotation in response to at least one of a change in the scope rotation of the first camera apparatus and an input to a user interface of one of the first camera apparatus and the second camera apparatus.

13. The imaging system according to claim 1, wherein the controller is further configured to:
adjust the rotation of the image data based on the camera orientation in conjunction with the scope orientation, wherein the rotation is adjusted to maintain a relationship of the scope orientation relative to the camera orientation presented in the image data.

14. A method for displaying image data from a plurality of surgical cameras, the method comprising:
receiving first image data from a first camera comprising a first video feed and second image data from a second camera comprising a second video feed;
receiving first camera orientation data from the first camera and second camera orientation data from the second camera; and
adjusting at least one of a first display rotation of the first image data and a second display rotation of the second image data, wherein a relationship between the first display rotation is maintained relative to the second display rotation based on one of the first camera orientation data and the second camera orientation data.

15. The method according to claim 14, wherein the first display rotation of the first video feed is maintained relative to gravity and the relationship between the first display rotation and the second display rotation of the second video feed is maintained at a fixed angle.

16. The method according to claim 15, further comprising:
updating the fixed angle between the first display rotation and the second display rotation in response to an input to a user interface of the first camera or the second camera.

17. The method according to claim 14, further comprising:
receiving a scope angle indicating an angular relationship between an angled scope and a camera body of the first camera; and
adjusting a first image rotation of the first image data in response to a change in the scope angle.

18. The method according to claim 14, wherein the first display rotation of the first video feed is maintained relative to a user-defined direction and the relationship between the first display rotation and the second display rotation of the second video feed is maintained at a user-defined offset.

19. The method according to claim 14, wherein the user-defined direction is offset relative to at least one of a fixed bearing or direction of gravity.

20. A surgical imaging system comprising:
a first camera apparatus comprising a first camera body including a first image sensor configured to capture first image data in a first field of view, wherein the first camera apparatus comprises a first camera orientation sensor configured to capture first camera orientation data of the first camera apparatus;
a second camera apparatus comprising a second camera body including a second image sensor configured to capture second image data in a second field of view, wherein the second camera apparatus comprises a second camera orientation sensor configured to capture second camera orientation data of the second camera apparatus;
a controller in communication with the first camera apparatus and the second camera apparatus, the controller configured to:
receive the first image data and the second image data;
receive the first camera orientation data and the second camera orientation data;
generate first display data at a first display angle from the first image data and second display data at a second display angle from the second image data and adjust the second display data to maintain a relationship between the first display angle and the second display angle; and
selectively control a display of a first video feed of the first image data or a second video feed of the second image data in response to the first camera orientation data and the second camera orientation data.

21. The surgical imaging system according to claim 20, further comprising:
a user interface in communication with the controller, and wherein the controller is further configured to:
update the relationship between the first display angle and the second display angle in response to an input to the user interface.

22. The surgical imaging system according to claim 20, wherein the
selective control of the first video feed and the second video feed is selected by the controller in response to a relationship between the first camera and the second camera relative to gravity.

23. The imaging system according to claim 20, wherein at least one of the first camera and the second camera comprise:
- an elongated scope extending along a longitudinal axis and comprising a distal tip directed at a scope angle; and
- a scope rotation sensor configured to detect a scope rotation of the scope angle of the elongated scope relative to one of the first camera and the second camera, where the controller is further configured to adjust the relationship between the first display angle and the second display angle in response to the scope angle.

* * * * *